United States Patent

Failli et al.

[11] Patent Number: 5,830,911
[45] Date of Patent: Nov. 3, 1998

[54] PYRANOINDOLE AND TETRAHYDROCARBAZOLE INHIBITORS OF COX-2

[75] Inventors: Amedeo A. Failli, Princeton Junction, N.J.; Robert J. Steffan; Anthony F. Kreft, both of Langhorne, Pa.; Thomas J. Caggiano, Morrisville, Pa.; Craig E. Caufield, Princeton Junction, N.J.

[73] Assignee: American Home Products Corporation, Madison, N.J.

[21] Appl. No.: 906,361

[22] Filed: Aug. 5, 1997

Related U.S. Application Data

[60] Provisional application No. 60/023,938 Aug. 14, 1996.
[51] Int. Cl.$^6$ .......................... A61K 31/40; C07D 209/86
[52] U.S. Cl. ............................................ 514/411; 548/449
[58] Field of Search .............................. 548/449; 514/411

[56] References Cited

FOREIGN PATENT DOCUMENTS 0300676  1/1989  European Pat. Off. .
0310179  4/1989  European Pat. Off. .

OTHER PUBLICATIONS

Huang et al, Exp. Opin. Invest. Drugs, Cyclooxygenase and 5–lipoxygenase inhibitors for the prevention and treatment of cancer, (1995) 4(3):243–249.
Rogers et al., Neurology, Clinical trial of indomethacin in Alzheimer's disease, (1993) 43:1609–1611.
Sano et al., Cancer Res., Expression of Cyclooxygenase–1 and –2 in Human Colorectal Cancer, (1995) 55:3785–3789.

Primary Examiner—Patricia L. Morris
Attorney, Agent, or Firm—Arnold S. Milowsky

[57] ABSTRACT

This invention provides compounds of formula I having the structure

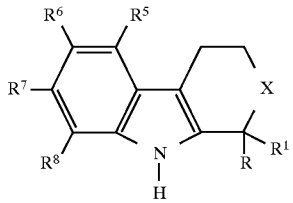

wherein

R is $(CH_2)_n COOR^4$;

$R^1$ is hydrogen, alkyl, alkenyl, alkynyl, alkylcycloalkyl, and alkoxyalkyl;

$R^4$ is hydrogen or alkyl;

$R^5$, $R^6$, $R^7$, and $R^8$ are each, independently, hydrogen, halogen, alkyl, alkenyl, alkynyl, alkoxy, arylalkoxy, fluoroalkoxy, alkylthio, alkylsulfinyl, alkylsulfonyl, cyano, nitro, —$SCF_3$, —$COR^3$, alkanoyloxy, hydroxy, trifluoromethyl, amino, alkylamino, dialkylamino, alkylamido, or alkylsulfonamido; wherein at least one of $R^5$, $R^6$, $R^7$, or $R^8$ is cyano;

$R^3$ is alkyl, hydroxy, alkoxy, amino, alkylamino;

X is —O— or —C—; and n=1–4 or a pharmaceutically acceptable salt thereof, which are useful in the treatment of arthritic disorders, colorectal cancer, and Alzheimer's disease.

14 Claims, No Drawings

PYRANOINDOLE AND TETRAHYDROCARBAZOLE INHIBITORS OF COX-2

This application claims the benefit of U.S. Provisional Application Ser. No. 60/023,938, filed Aug. 14, 1996.

FIELD OF THE INVENTION

This invention is in the fields of antiinflammatory and anticancer pharmaceutical agents and specifically relates to compounds, compositions and methods for treating inflammation and inflammation-associated disorders, such as arthritis and Alzheimer disease, and for the treatment and/or prevention of cycloxygenase-mediated disorders such as may occur in diabetic retinopathy and tumor angiogenesis. More particularly, they may prove useful in certain types of cancer growth, such as colorectal cancer and in the treatment of Alzheimer disease.

BACKGROUND OF THE INVENTION

Prostaglandins have been known for some time to play a major role in the inflammation process, and have been shown to be involved in the pathophysiology of several chronic human diseases. They are involved as mediators of pain, edema and vascular permeability in arthritic diseases such as rheumatoid arthritis and osteoarthritis (Lewis and Kreft, *Immunopharmacol. Immunotoxicol.* 17, 607–663 (1995)). In addition, prostaglandins have been postulated to be involved in the pathophysiology of colorectal cancer (Marcus, *New Eng. J. Med.*, 333, 656–657 (1995); Huang and Heimbrook, *Exp.Opin. Invest. Drugs.*, 4 (3), 243–249 (1995)). Thus an agent that inhibits prostaglandin synthesis may be useful in treating these disorders.

The biosynthesis of prostaglandins was previously thought to be due to the action of a single cyclooxygenase enzyme on arachidonic acid to afford prostaglandin $H_2$ (Vane et al, *Postgrad. Med. J.*, 66 (Suppl 4), S2–S17 (1990); Lewis and Kreft, *Immunopharmacol. Immunotoxicol.* 17, 607–663 (1995)). This intermediate is subsequently transformed into the various members of the prostaglandin family by more distal enzymes. The clinical utility of cyclooxygenase inhibitors (often called NSAIDs; nonsteroidal antiinflammatory drugs) is well established in arthritic disorders (Brooks et al, *New Eng. J. Med.*, 324, 1716–1725 (1991)). However, these compounds also affect other prostaglandin-regulated processes not associated with inflammation but rather, with maintenance of gastrointestinal integrity and renal blood flow (Dajani et al. *J. Physiol. Pharmacol.*, 46, 3–16 (1995); Somasundaram et al. *Scand. J. Gastroenterol.*, 30, 289–299 (1995)), via a mechanism involving inhibition of prostaglandin G/H synthase or cycloxygenase (COX). Thus, at high doses often necessary to show therapeutic efficacy, most NSAIDs show severe gastric and renal side effects, including life threatening ulcers that limit their therapeutic utility. An alternative to NSAIDs is the use of corticosteroids, which have even more severe liabilities, especially when long term therapy is involved.

Under the old paradigm of a single cyclooxygenase enzyme, it appeared that the selective inhibition of prostaglandin synthesis in inflamed tissue versus inhibition of prostaglandin synthesis in G.I. tissue was unlikely unless tissue specificity could be achieved.

Recently, the discovery that there are two distinct cyclooxygenase isozymes in the arachidonic acid/prostaglandin pathway, has given rise to a new paradigm which may lead to compounds that have a separation of inhibition of prostaglandin synthesis in inflamed tissue from inhibition of prostaglandin synthesis in G.I. tissue (Hayllar, *Lancet,* 346, 521–522 (1995), Lewis and Kreft, *Immunopharmacol. Immunotoxicol.* 17, 607–663 (1995)). In the new paradigm the constitutive cyclooxygenase enzyme responsible for prostaglandin synthesis in G.I. tissue is termed COX-1 and the inducible cyclooxygenase enzyme (reported by Hla and Nielson, *Proc. Ntl. Acad. Sci. USA,* 89, 7384 (1992)) responsible for prostaglandin synthesis in inflamed tissue is termed COX-2. COX-1 appears to have a physiological role being involved in maintenance of gastrointestinal integrity and renal blood flow, while COX-2 appears to be mainly responsible for the pathological effects of prostaglandins.

Several groups have reported that NSAIDS vary in their ability to inhibit COX-1 and COX-2 so that selective inhibition may be possible (O'Neill et al, *Molec. Pharmacol.,* 45, 245–254 (1994); Laneuville et al, *J. Pharmacol. Exp. Ther.,* 271, 927–934 (1994); Mitchell et al, *Proc Natl. Acad. Sci. USA,* 90, 11693–11697 (1993)). The current opinion suggests that a selective inhibitor of COX-2 will have clinical efficacy in inflammatory diseases with reduced potential for gastrointestinal toxicity and renal side effects. There is evidence from animal models to support this hypothesis (Chan et. al *J. Pharmacol. Exp. Ther.* 274, 1531–1537 (1995); Masferrer et. al. *Proc. Natl. Acad. Sci. USA,* 91, 3228–3232 (1994); Seibert et al., *Proc. Natl. Acad. Sci. USA,* 91, 12013–12017 (1994)). Moreover, this may be the mechanism behind the improved G.I. safety of the NSAID etodolac, which has been reported to show a tenfold selectivity for inhibition of COX-2 (Glaser et al. *Eur. J. Pharmacol.* 281, 107–111 (1995)).

Indomethacin, a relatively non-selective inhibitor of COX-1 and COX-2 has been shown to be useful in the treatment of Alzheimer's disease (Rogers et al., *Neurology* 43, 1609–1611 (1993)). These findings suggest that novel COX-2 inhibitors would be attractive targets for the treatment of Alzheimer disease and for antiarthritic therapy with reduced potential for gastrointestinal toxicity and renal side effects. In addition, the COX-2 enzyme has been shown to be upregulated in colorectal cancer and a selective COX-2 inhibitor may also be of use in this disease (Sano et. al. *Cancer Res . . . ,* 55, 3785–3789 (1995); Huang and Heimbrook, *Exp. Opin. Invest. Drugs* 4 (3), 243–249, (1995)).

European Patent 300,676 discloses cyano substituted 9-substituted 1,2,3,4-tetrahydrocarbazole 1-alkanoic acids as prostaglandin and thromboxane antagonists, with antiinflammatory, antihypertensive and cytoprotective properties.

European Patent 310,179 discloses cyano substituted 9-substituted 1,2,3,4-tetrahydrocarbazole alkanoic acid esters prostaglandin and thromboxane antagonists, with antiinflammatory, antihypertensive and cytoprotective properties.

Each of the two European Patents documents cited above discloses compounds that are structurally different from the compounds of the present invention. In addition, the compounds of the present invention have been shown to be cycloxygenase inhibitors, and were unexpectedly found to exhibit marked selectivity for the inhibition of COX-2 over COX-1. The compounds disclosed in each of the documents cited above unlike the compounds of the present invention, do not act as preferential inhibitors of COX-2; thus, they are not expected to exhibit any of the advantages of the compounds of the present invention, i.e. they are not expected to produce a reduced mount of side effects.

DESCRIPTION OF THE INVENTION

In accordance with this invention, there are provided COX-2 inhibitors which are useful as antiarthritic, anticancer and anti-Alzheimers agents of formula I:

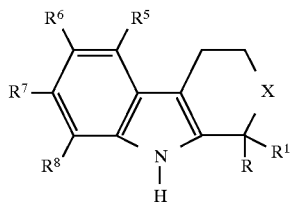

wherein

R is $(CH_2)_n COOR^4$;

$R^1$ is hydrogen, alkyl of 1–6 carbon atoms, alkenyl of 2–7 carbon atoms, alkynyl of 2–7 carbon atoms, alkylcycloalkyl of 4–14 carbon atoms, and alkoxyalkyl of 2–12 carbon atoms;

$R^4$ is hydrogen or alkyl of 1–6 carbon atoms;

$R^5$, $R^6$, $R^7$, and $R^8$ are each, independently, hydrogen, halogen, alkyl of 1–6 carbon atoms, alkenyl of 2–7 carbon atoms, alkynyl of 2–7 carbon atoms, alkoxy of 1–6 carbon atoms, arylalkoxy of 7–12 carbon atoms, fluoroalkoxy of 1–6 carbon atoms, alkylthio of 1–3 carbon atoms, alkylsulfinyl of 1–3 carbon atoms, alkylsulfonyl of 1–3 carbon atoms, cyano, nitro, —$SCF_3$, —$COR^3$, alkanoyloxy of 2–6 carbon atoms, hydroxy, trifluoromethyl, amino, alkylamino of 1–6 carbon atoms, dialkylamino in which each alkyl moiety is of 1–6 carbon atoms, alkylamido of 2–7 carbon atoms, or alkylsulfonamido of 1–6 carbon atoms; wherein at least one of $R^5$, $R^6$, $R^7$, or $R^8$ is cyano;

$R^3$ is alkyl of 1–6 carbon atoms, hydroxy, alkoxy of 1–6 carbon atoms, amino, alkylamino of 1–6 carbons or dialkylamino in which each alkyl moiety is of 1–6 carbon atoms;

X is —O— or —C—; and n=1–4 or a pharmaceutically acceptable salt thereof.

Some of the compounds of this invention contain one or more asymmetric centers and may thus give rise to optical isomers and diastereomers. The present invention includes such optical isomers and diastereomers; as well as the racemic and resolved, enantiomerically pure R and S stereoisomers; as well as other mixtures of the R and S stereoisomers and pharmaceutically acceptable salts thereof.

The terms alkyl, alkenyl, and alkynyl include both straight chain as well as branched moieties. This includes the alkyl portions of substituents such as alkoxy, alkylthio, alkylamino, and the like. The term halo includes fluorine, chlorine, bromine, and iodine. Fluoroalkoxy includes mono-, di-, tri-, and polyfluorinated alkoxy moieties such as —$OCF_3$, —$OCH_2F$, —$OCHF_2$, —$CH_2CF_3$, and the like.

The aryl moiety of the aryloxy substituent includes phenyl or heteroaryl radicals, which may be optionally substituted with halogen, alkyl of 1–6 carbon atoms, alkoxy of 1–6 carbon atoms, cyano, hydroxy, nitro, carbalkoxy of 2–7 carbon atoms, $CF_3$, fluoroxalkoxy, amino, alkylamino of 1–6 carbon atoms, dialkylamino in which each alkyl moiety is of 1–6 carbon atoms, alkylamido of 2–7 carbon atoms, or alkylsulfonamido of 1–6 carbon atoms, alkoxyalkyl of 2–12 carbon atoms, alkylthio of 1–6 carbon atoms, or —$CO_2H$. The term heteroaryl includes monocyclic aromatic 5-membered ring containing one to three heteroatoms selected from the group consisting of O, N, or S; or a monocyclic 6-membered aromatic ring containing one or two nitrogens. Preferred heterocyclic radicals include furyl, thiophenyl, pyrrolyl, pyrazolyl, imidazolyl, 1,2,3-triazolyl, 1,2,4-triazolyl, isoxazolyl, oxazolyl, thiazolyl, isothiazolyl, 1,2,4-oxadiazolyl, 1,2,5-oxadiazolyl, 1,3,4-oxadiazolyl, 1,2,4-thiadiazolyl, 1,3,4-thiadiazolyl, 1,2,5-thiadiazolyl, 1,2,3-thiadiazolyl, pyridinyl, pyridazinyl, pyrimidinyl, and pyrazinyl.

Preferred compounds of this invention include those in which $R^1$ is alkyl of 1–6 carbon atoms or alkenyl of 2–7 carbon atoms; those in which $R^1$ is alkyl of 1–6 carbon atoms or alkenyl of 2–7 carbon atoms and n=1; and those in which $R^1$ is alkyl of 1–6 carbon atoms or alkenyl of 2–7 carbon atoms, n=1, and $R^5$ is cyano.

The pharmaceutically acceptable salts are those derived from such organic and inorganic acids as acetic, lactic, citric, tartaric, succinic, fumaric, maleic, malonic, mandelic, malic, hydrochloric, hydrobromic, phosphoric, nitric, sulfuric, methanesulfonic, toluenesulfonic and similarly known acceptable acids.

The cyano 2,3,4,9-tetrahydro-1H-carbazole-1-alkanoic acids of the present invention are preferably prepared by Fischer indole synthesis as shown in Scheme I using an appropriately substituted cyclohexanone of formula (III) with a bromo substituted phenylhydrazine of formula (II) wherein $R^6$, $R^7$ and $R^8$ are as defined above. For a review of indole syntheses similar to those utilized in the present invention see B. Robinson, *The Fischer Indole Synthesis*, Wiley, New York, (1983); and R. D. Clark and D. B. Repke, *Heterocycles*, 22, 195–220 (1984).

The intermediate phenylhydrazone of formula (IV) is cyclized by treatment with boron trifluoride etherate in glacial acetic acid to provide the bromoester of formula (V). Displacement of the bromine with cyanide is accomplished by heating the bromo ester of formula (V) with copper (I) cyanide in N-methyl pyrrolidone. Alternatively, the conversion of the aryl bromide to aryl cyanide can be accomplished by treatment with zinc cyanide and a catalytic amount of tetrakis(triphenylphosphine)palladium(O) according to the procedure of Tschaen et al., *Synth. Comm.*, 24, 887–890 (1994). The hydrolysis of the cyano ester intermediates of formula (VI) is conveniently carried out by using NaOH (KOH or LiOH) in aqueous methanol (ethanol or THF) followed by acidification to obtain compounds of formula (1).

Scheme I

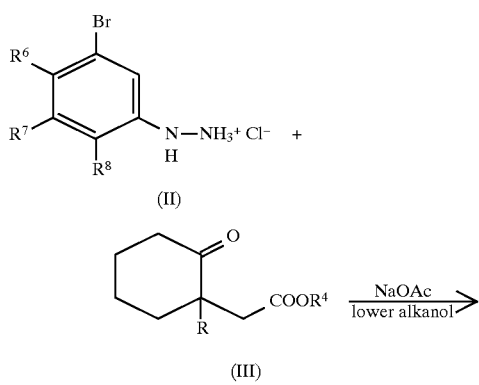

-continued
Scheme I

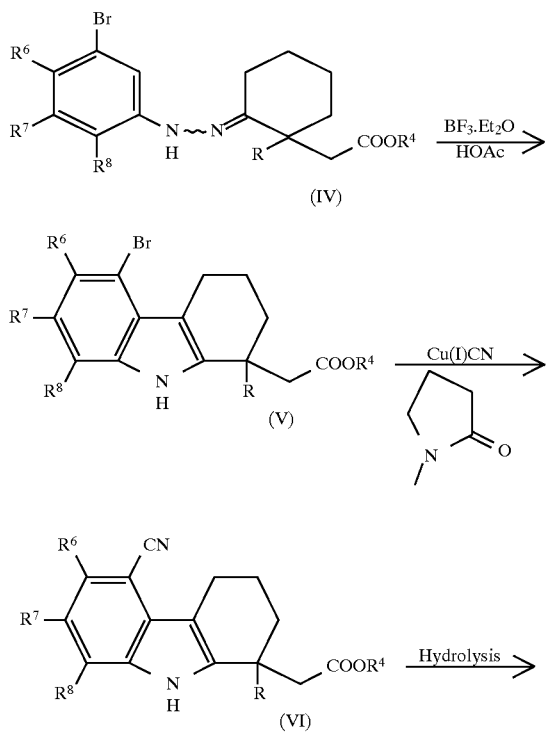

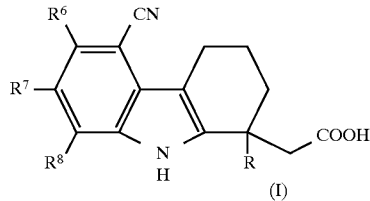

The substituted cyclohexanone of formula (III) can be conveniently prepared according to the procedure of Asselin et al., *J. Med. Chem.* 19, 787–792, (1976). The appropriately substituted phenylhydrazines of formula (It) are available commercially or are known in the art or can be readily prepared by procedures analogous to those in the literature for the known compounds.

When two bromine substituents are present as it is the case in the intermediate dibromo ester of formula (Va, $R^8$=Br) displacement of the bromine substituents with copper (I) cyanide in N-methyl pyrrolidone (or with zinc cyanide and a catalytic amount of Pd (0)) as described above), provides the dicyano ester of formula (VIa, $R^8$=CN). Hydrolysis of the dicyano ester of formula (VIa) with LiOH (KOH or NaOH) in aqueous methanol (ethanol or THF) followed by acidification, may in certain cases provide in addition to the dicyano acid of formula (Ia, $R^8$=CN) also a cyano carboxamido acid of formula (Ib, $R^8$=CONH$_2$) as shown in Scheme II. The two acids of formula (Ia, $R^8$=CN) and (Ib, $R^8$=CONH$_2$) can be conveniently separated by crystallization of the reaction mixture followed by preparative HPLC of the mother liquors of recrystallization, respectively as shown in Scheme II.

Scheme II

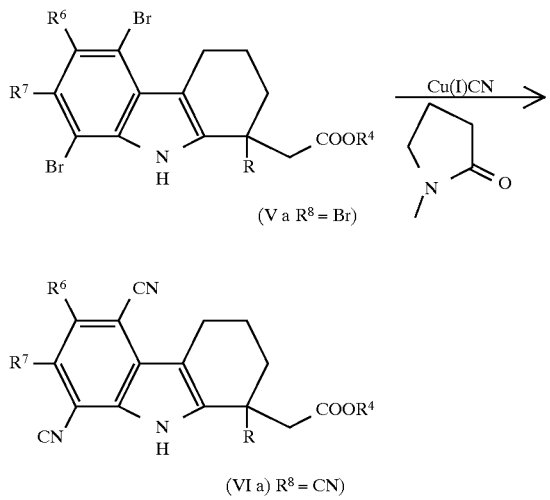

-continued
Scheme II

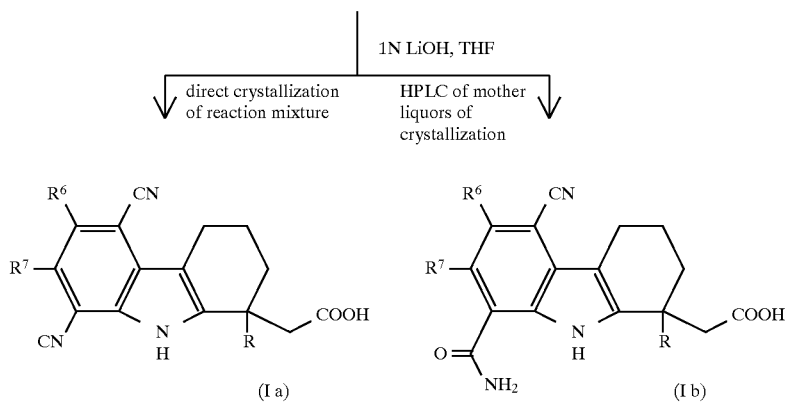

When the substituent $R^8$ is hydrogen as it is the case in the intermediate bromo phenylhydrazone of formula (IVc, $R^6$, $R^7$ and $R^8$=H) the Fischer indole cyclization provides two regioisomeric bromoesters of formula (Vc, $R^5$=Br; $R^6$, $R^7$ and $R^8$=H) and (Vd, $R^7$=Br; $R^5$, $R^6$ and $R^8$=H) respectively, as shown in Scheme III. Displacement of the bromine substituent with copper (I) cyanide in N-methyl pyrrolidone (or with zinc cyanide and a catalytic amount of Pd (0)) as described above, is carried out on the mixture of bromoesters of formula (Vc) and (Vd) described above to provide a mixture of regioisomeric cyano esters of formula (VIc, $R^5$=CN; $R^6$, $R^7$ and $R^8$=H) and (VId, $R^7$=CN; $R^5$, $R^6$ and $R^8$=H), which is in turn hydrolyzed with aqueous LiOH (KOH or NaOH) in a lower alkanol (or THF). The regioisomeric acids of formula Ic ($R^5$=CN; $R^6$, $R^7$ and $R^8$=H) and Id ($R^7$=CN; $R^5$, $R^6$ and $R^8$=H) can be conveniently separated by crystallization of the reaction mixture followed by preparative HPLC of the mother liquors of recrystallization, respectively as shown in Scheme III.

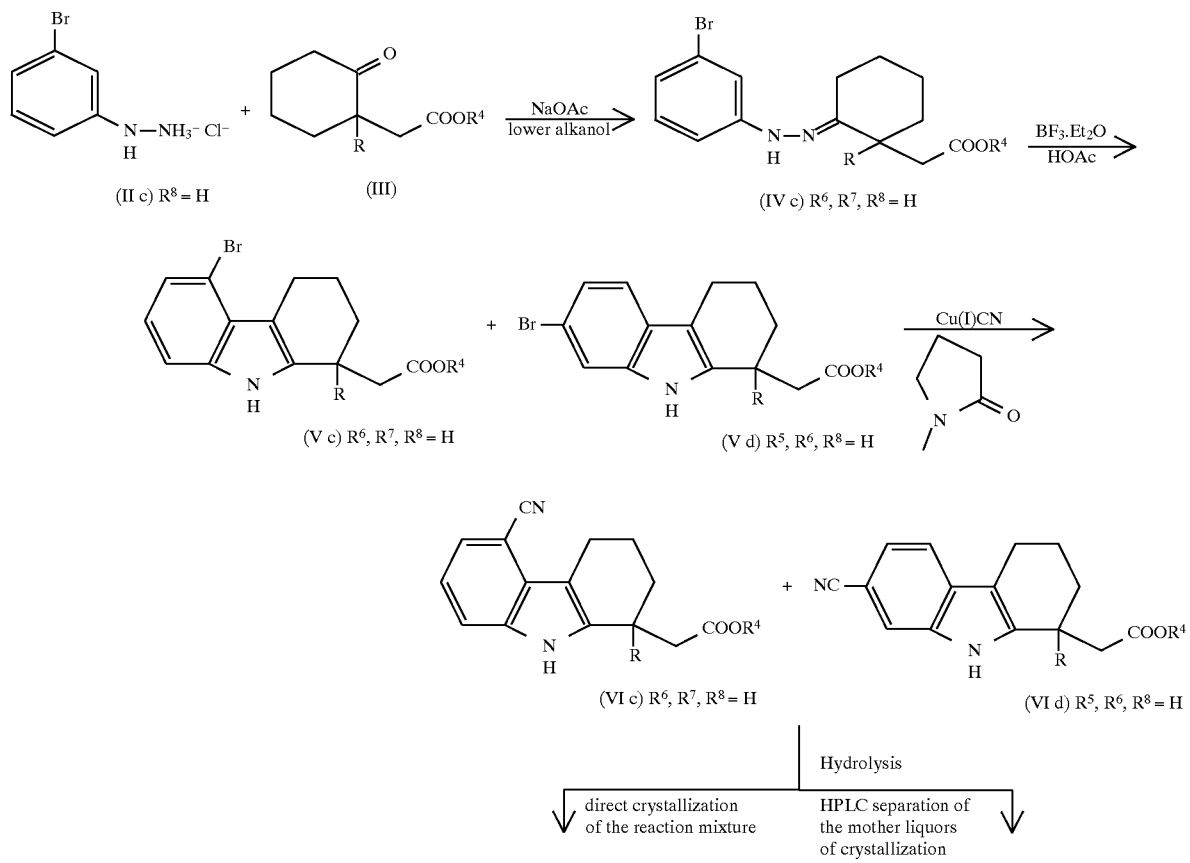

-continued
Scheme III

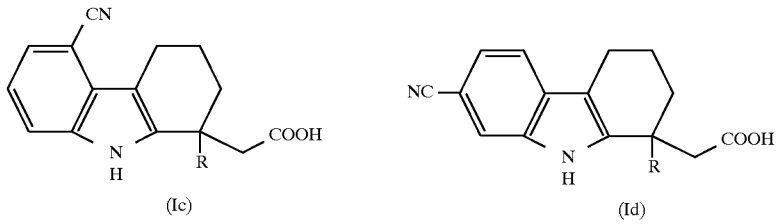

(Ic)                                  (Id)

The cyano 1,3,4,9-tetrahydropyrano[3,4-b]indole-1-alkanoic acids of the present invention are preferably prepared by Fischer indole synthesis as shown in Scheme IV, by reacting dihydrofuran with an appropriately substituted phenylhydrazine of formula (II) wherein $R^6$, $R^7$ and $R^8$ are as defined above. The intermediate substituted phenylhydrazone of formula VII (mixture of E and Z isomers) is cyclized by heating in ethylene glycol in presence of $ZnCl_2$ to provide the substituted bromotryptophol of formula (VIII). Cyclization of the intermediate bromotryptophol of formula (VIII) to the bromo-1,3,4,9-tetrahydropyrano[3.4-b]indole of formula (X) is accomplished by treatment of (VIII) with an enolether ester of formula (IX) in presence of a Lewis acid such as boron trifluoride etherate. Displacement of the bromine substituent with cyanide is accomplished by heating the bromo ester of formula (X) with copper (I) cyanide in N-methyl pyrrolidone (or with zinc cyanide and a catalytic amount of Pd (0)) as described above. The hydrolysis of the resulting cyano ester intermediate of formula (XI) is conveniently carried out by using aqueous NaOH (KOH or LiOH) in methanol (ethanol or THF) followed by acidification to obtain compounds of formula (Ie).

Scheme IV

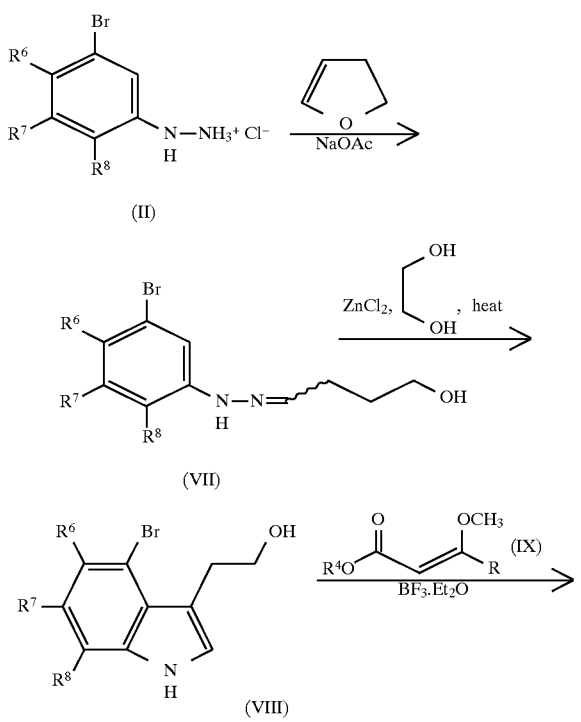

-continued
Scheme IV

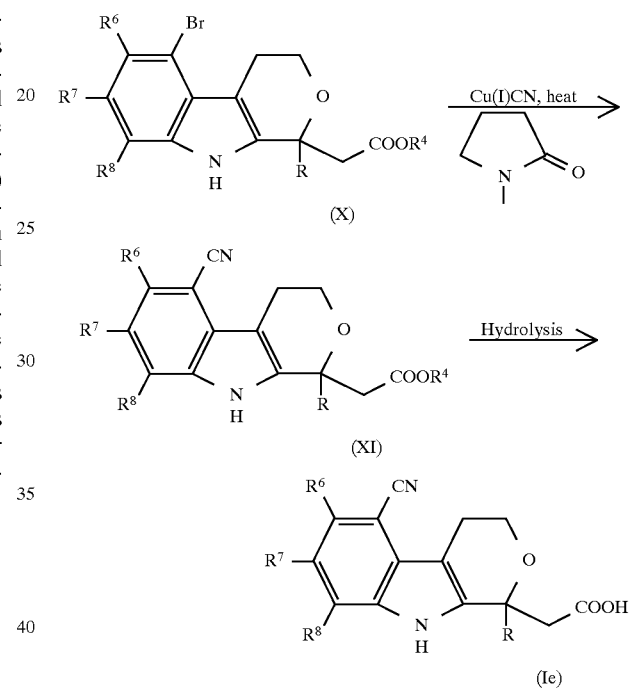

When the substituent $R^8$ is hydrogen as it is the case with the intermediate bromophenylhydrazone of formula VIIf, ($R^6$, $R^7$ and $R^8$=H) the Fischer indole cyclization provides a 1:1 mixture of regioisomeric 4- and 6-bromo tryptophols of formula (VIIIf, $R^5$=Br; $R^6$, $R^7$ and $R^8$=H) and (VIIIg, $R^7$=Br; $R^5$, $R^6$ and $R^8$=H) respectively, as shown in Scheme V. The mixture of tryptophols (VIIIf) and (VIIIg) is cyclized under the conditions described above to a 1:1 mixture of regioisomeric bromoesters of formula Xf ($R^5$=Br; $R^6$, $R^7$ and $R^8$=H) and Xg ($R^7$=Br; $R^5$, $R^6$ and $R^8$=H). Separation of the individual regioisomers (Xf) and (Xg) can be conveniently accomplished by a combination of chromatography and recrystallization. The individual regioisomeric bromoesters (Xf) and (Xg) can be each independently converted to the corresponding cyanoesters XIf ($R^5$=CN; $R^6$, $R^7$ and $R^8$=H) and XIg ($R^7$=CN; $R^5$, $R^6$ and $R^8$=H), which are in turn each independently hydrolyzed with aqueous LiOH (KOH or NaOH) in a lower alkanol (or THF) to the corresponding acids (If) and (Ig).

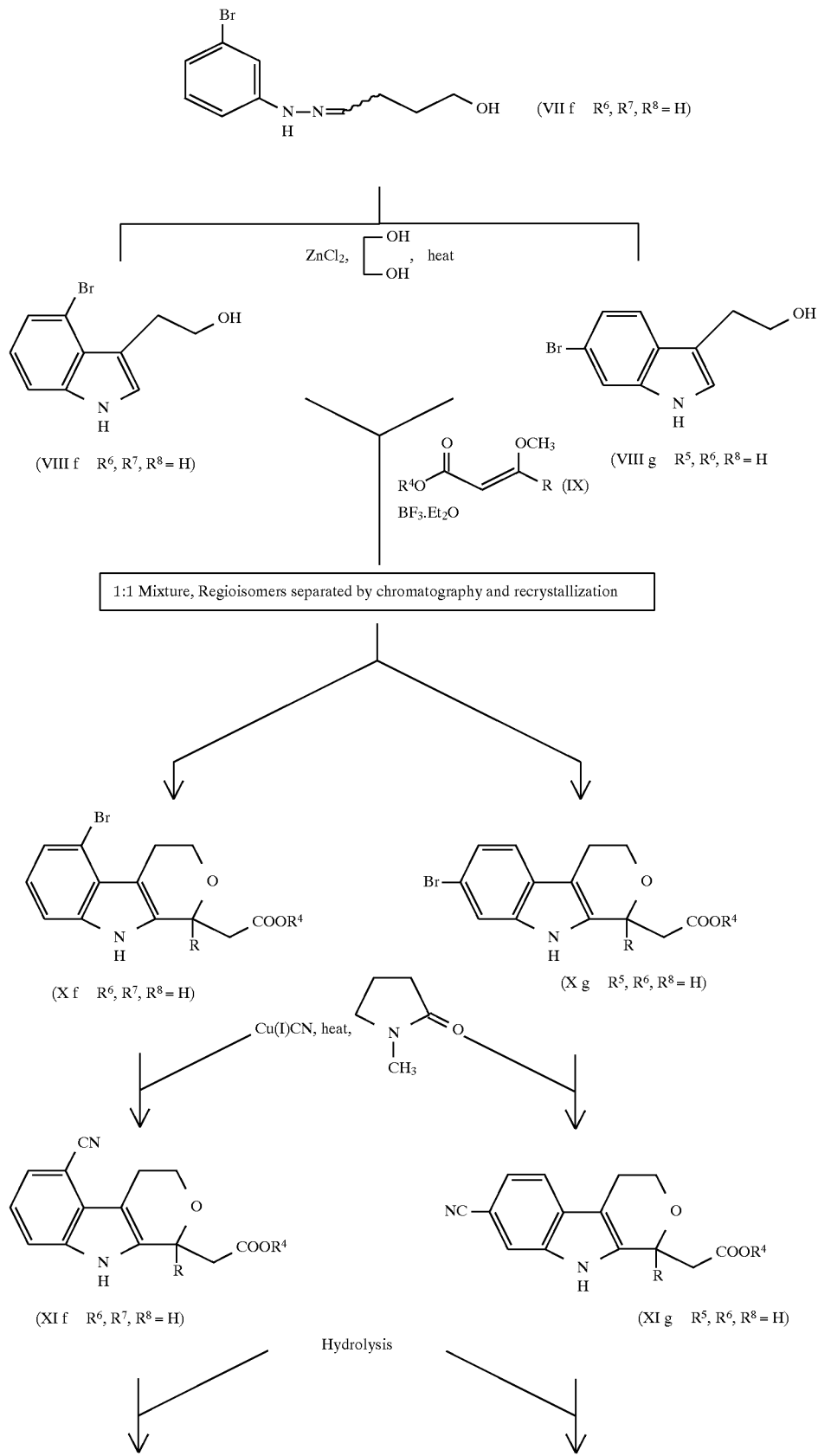

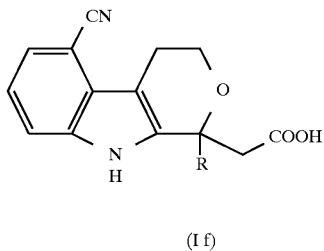

(I f)

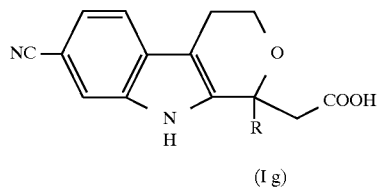

(I g)

Alternatively, a more efficient, regiospecific preparation of the 4-bromo tryptophol of formula (VIIIf, $R^6$ and $R^7$ are as defined above and $R^8$=H) can be accomplished by the Leimgruber-Batcho indole cyclization as shown in Scheme VI. The 2-bromo-6-nitro toluene of formula (XII) is converted to the 4-bromoindole of formula (XIII, $R^8$=H) by a procedure essentially analogous to that described by Rapoport et al., *J. Org. Chem.*, 51, 5106–5110 (1986). The intermediate bromoindole of formula (XIII) is then converted to the 4-bromo tryptophol of formula (VIIIf, $R^8$=H) by procedures analogous to those in the literature for the known compounds.

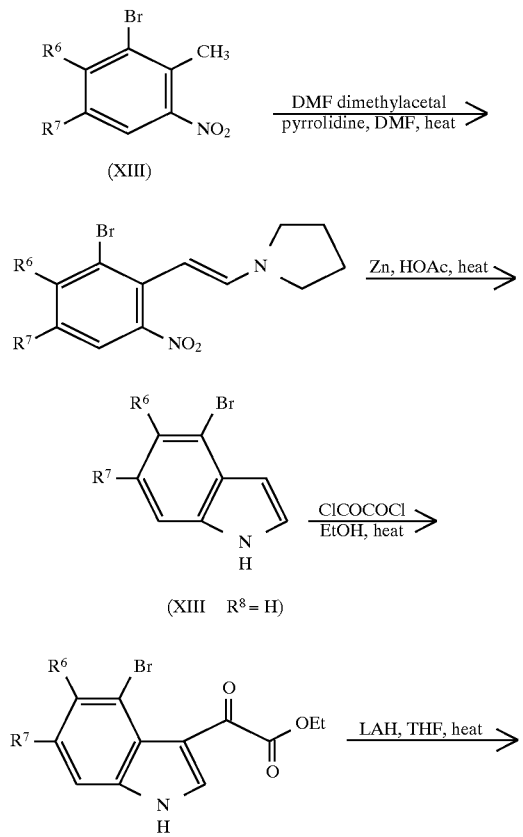

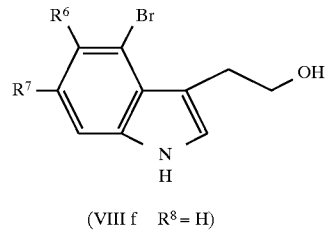

(VIII f  $R^8$= H)

The compounds of the present invention inhibit the COX-2 enzyme (Tables 1 and 2) believed to be responsible for the production of high levels of prostaglandins in inflammation and certain types of cancer, such as colorectal cancer. It has been shown that preferential inhibition of the COX-2 enzyme relative to COX-1 inhibition leads to an anti inflammatory effect with substantially reduced G.I. toxicity (Chan et al, *J. Pharmacol. Exp. Ther.* 274, 1531–1537 (1995); Masferrer et al. *Proc. Natl. Acad. Sci. USA*, 91, 3228–3232 (1994); Seibert et al,, *Proc. Natl. Acad. Sci. USA*, 91, 12013–12017 (1994)). Futaki et al. (*Gen. Pharmac.* 24, 105–110, 1993) have reported that a selective COX-2 inhibitor N-(2-cyclohexyloxy-4-nitrophenyl)methanesulfonamide is an effective antiinflammatory and lacks gastric side effects. Therefore, the compounds of this invention by virtue of their inhibition of cyclooxygenase-2 and/or their specificity for cyclooxygenase-2 over cyclooxygenase-1, are for the treatment of inflammatory diseases such as rheumatoid arthritis and Alzheimer disease, and of certain types of cancer particularly in patients with peptic ulcers, gastric lesions and other gastric disorders because of their safer profile.

Representative compounds of this invention were evaluated for inhibition of COX-2 and COX-1 enzymes as follows. Human COX-1 and COX-2 cDNAs were cloned from human monocytes, untreated and LPS-treated respectively, by RT-PCR using oligonucleotide primers based on published hCOX-1 and hCOX-2 sequences (Jones et al., *J. Biol. Chem.*, 268, 9049 (1993)). The cDNAs were then transfected into either Sf9 or CHO cells and subsequently converted into a microsomal preparation as described by Glaser et al (*Eur. J. Pharmacol.* 281, 107–111 (1995)). The microsomal human recombinant enzymes were diluted with buffer (100 mM Tris, pH 7.8 at 37° C.) containing 0.5 mM phenol (964 ml total volume). The enzyme preparations were preincubated with vehicle (DMSO) or compounds in DMSO (1 % DMSO in final assay) for 30 min at 37° C. Excess hematin was added 1 min prior to initiation of reaction (1.25 mM final hematin) with 30 mM arachidonic acid (sodium salt). Final assay volume was 1.0 ml (100 mM Tris (pH 7.8), 0.5 mM phenol, 1.25 mM hematin and 30 mM arachidonic acid at 37° C.).

The reaction was incubated for 35 sec (maximum level of $PGH_2$ accumulation as determined from time course studies), and terminated by addition of 50–60 mL of $SnCl_2$ (1 mg/ml) in 0.1N HCl. $PGH_2$ is quantitatively converted to $PGF_{2\alpha}$ by this reaction (50% efficiency of total conversion). The pH of each tube is adjusted to pH 3.0–3.5 with 0.1N— NaOH and extracted twice with 1.5 ml of ethyl acetate (75–90% efficiency per extraction). Combined ethyl acetate extracts were dried under $N_2(g)$ and redissolved in EIA buffer (2.0 ml), and $PGF_{2\alpha}$ ( was quantified by EIA.

In all cases it has been found that similar results are obtained with either the recombinant human COX-1 or the purified ovine COX-1 enzymes, as reported in the literature (R. A. Copeland et al., *Proc. Natl. Acad. Sci. USA*, 91, (1994)). Accordingly, all the COX-1 data reported here are for the purified ovine COX-1 enzyme which was purchased from Cayman Chemicals (Ann Arbor, Mich.).

The results of the standard pharmacological test procedure described in the preceding paragraphs are shown below.

TABLE 1

Inhibition of rhCOX-2 and purified ovine COX-1 by cyano 1,3,4,9-tetrahydropyrano[3,4-b]indoles

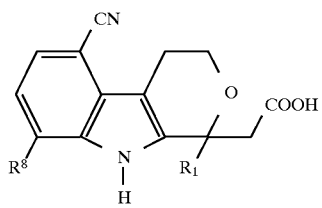

| Example | $R^8$ | $R^1$ | % inh of rhCOX-2 ($IC_{50}$, $\mu M$) | % inh of pur. bovine COX-1 ($IC_{50}$, $\mu M$) |
|---|---|---|---|---|
| 1 | F | n-Pr | (1) | |
| 2 | $CH_3$ | n-Pr | 38 at 3 $\mu M$ | 86 at 90 $\mu M$ |
| 3 | H | ethyl | (0.57) | 47 at 30 $\mu M$; 31 at 270 $\mu M$ |
| 4 | H | n-Pr | (1.7) | (>1000) |

TABLE 2

Inhibition of rhCOX-1 and purified ovine COX-2 by cyano 2,3,4,9-tetrahydro-1H-carbazoles

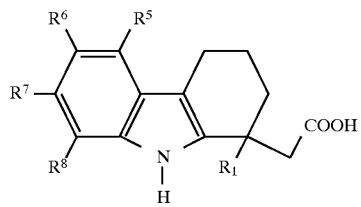

| Example | $R^5$ | $R^6$ | $R^7$ | $R^8$–$R^1$ | | % inh of rhCOX-2 ($IC_{50}$, $\mu M$) | % inh of pur. bovine COX-1 ($IC_{50}$, $\mu M$) |
|---|---|---|---|---|---|---|---|
| 5 | CN | H | F | allyl | H | (0.1) | 93 at 10 $\mu M$ |
| 6 | CN | H | F | n-Pr | H | (0.32) | 73 at 10 $\mu M$ |
| 7 | CN | H | $CH_3$ | allyl | H | 75 at 0.3 $\mu M$ | 99 at 30 $\mu M$ |
| 8 | CN | H | $CH_3$ | n-Pr | H | 44 at 1 $\mu M$ | 99 at 270 $\mu M$ |
| 9 | CN | H | $CONH_2$ | n-Pr | H | 21 at 0.1 $\mu M$ | -37 at 90 $\mu M$ |

TABLE 2-continued

Inhibition of rhCOX-1 and purified ovine COX-2 by cyano 2,3,4,9-tetrahydro-1H-carbazoles

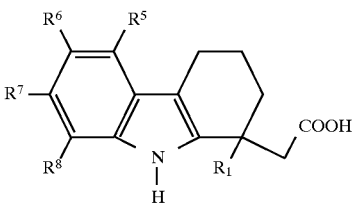

| Example | $R^5$ | $R^6$ | $R^7$ | $R^8$–$R^1$ | | % inh of rhCOX-2 ($IC_{50}$, $\mu M$) | % inh of pur. bovine COX-1 ($IC_{50}$, $\mu M$) |
|---|---|---|---|---|---|---|---|
| 10 | CN | H | H | n-Pr | H | 18 at 0.1 $\mu M$ | 74 at 90 $\mu M$ |
| 11 | CN | H | CN | allyl | H | 91 at 1 $\mu M$ | 86 at 270 $\mu M$ |
| 12 | CN | H | CN | n-Pr | H | 78 at 1 $\mu M$ | 98 at 270 $\mu M$ |
| 13 | H | CN | H | n-Pr | H | 31 at 0.1 $\mu M$ | 100 at 90 $\mu M$ |

The results obtained for representative compounds of this invention in the standard pharmacological test procedures demonstrated high inhibition of the human COX-2 isozyme. Based on the results obtained in this test procedure, the compounds of this invention are useful for the treatment of arthritic disorders, Alzheimer disease and colorectal cancer. Several compounds of the present invention also demonstrated high selectivity for the inhibition of the human COX-2 isozyme and would be expected to have a greater margin of G.I. safety The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets, preferably, contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount of therapeutically active compound that is administered and the dosage regimen for treating a specific arthritic disorder or colorectal cancer with the compound and/or compositions of this invention depends on a variety of factors, including the weight, age, sex, medical condition of the subject, the severity of the disease, the route and frequency of administration, and the specific compound employed, and thus may vary widely. The pharmaceutical compositions may contain active ingredient in the range of 0.1 to 2000 mg, preferably in the range of 0.5 to 500 mg and most preferably between 1 and 100 mg. Projected daily dosages of active compound are 0.01 to 100 mg/kg body weight. The daily dose of can be administered in one to four doses per day.

The following examples illustrate the preparation of representative compounds of this invention.

EXAMPLE 1

5-Cyano-8-fluoro-1-propyl-1 3,4,9-tetrahydropyrano [3,4-b]indole-1-acetic acid

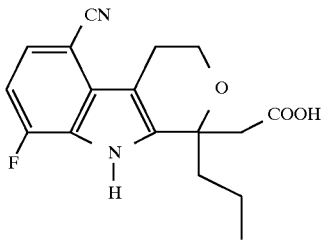

Step A. 4-(5-Bromo-2-fluorophenylhydrazono)-1-butanol

Under anhydrous conditions a solution of 5-bromo-2-fluoro-phenylhydrazine hydrochloride (3.5 g, 14.5 mmol) and 2,3-dihydrofuran (1.1 mL, 14.5 mmol) in 50 mL of dry THF was stirred at ambient temperature for 3 h. The reaction mixture was partitioned between EtOAc and $H_2O$. The organic phase was washed with $H_2O$ and brine and dried ($Na_2SO_4$). The solvent was evaporated to give 3.5 g of the title product as a brown oil (mixture of E/Z isomers). The product was of suitable purity for use in the next step.

NMR (DMSO-$d_6$, 300 MHz): δ 1.62 (m, 2H, $CCH_2C$), 2.25 (m, 2H, $CHCH_2$), 3.42 (m, 2H, $CH_2OH$), 4.42 (broad, 1H, OH), 6.8 (m, 1H, vinyl H), 7.05 (m, 1H, ArH), 7.35 (m, 1H, ArH), 7.475 (d, 1H, ArH), 9.825 (s, 1H, NH).

Step B. 4-Bromo-7-fluoro tryptophol

Under an atmosphere of nitrogen, a mixture of the crude hydrazone of Step A (11.6 g, 42 mmol) and zinc chloride (11.5 g, 84.3 mmol) in 50 mL of ethylene glycol was heated at 160° C. for 3 h. Upon cooling the reaction mixture was partitioned between $Et_2O$ and dilute HCl. The organic phase was washed with $H_2O$ and brine and dried ($Na_2SO_4$). The solvent was evaporated to give the crude product as a brown oil. Flash chromatography (silica Merck 60, hexane-EtOAc 2:1) gives 3.0 g of partially purified product as an amber oil. This crude material contained approximately 10% impurity (by NMR) and it was used as such in the next step.

NMR (DMSO-$d_6$, 300 MHz): δ 3.05 (t, 2H, $ArCH_2C$), 3.65 (m, 2H, $OCH_2C$), 4.6 (t, 1H, OH), 6.825 (m, 1H, ArH), 7.1 (m, 1H, ArH), 7.3 (s, 1H, ArH), 11.69 (s, 1H, NH).

Step C. 5-Bromo-8-fluoro-1-propyl-3,4,9-tetrahydropyrano [3,4-b]indole-1-acetic acid ethyl ester Under anhydrous conditions, a solution of the tryptophol of Step B (2.9 g, 11.2 mmol) and ethyl 3-methoxy-2-hexenoate (1.8 g, 11.5 mmol) in 50 mL of dry $CH_2Cl_2$ was treated dropwise with boron trifluoride etherate (1.4 mL, 11.5 mmol) via syringe. The solution was stirred at ambient temperature overnight and then washed with saturated aqueous $NaHCO_3$ and brine. Upon drying ($Na_2SO_4$), the organic phase was filtered through a pad of silica gel 60 (Merck). The filter cake was washed with additional $CH_2Cl_2$ and the combined organic phase was evaporated to provide 3.5 g of the title compound as a yellow oil which solidified on standing.

NMR (DMSO-$d_6$, 200 MHz): δ 0.8 (m, 3H, $CCH_3$), 0.9 and 1.25 (m, 2H, $CCH_2C$), 1.05 (t, 3H, $OCH_2CH_3$), 1.9 (m, 2H, $CH_2C$), 2.75 (d, 1H, $CCH_2CO$), 2.95 (m, 2H, $CCH_2$), 3.0 (d, 1H, $CCH_2CO$), 3.9 (m, 4H, $CCH_2O$), 693 (m, 1H, ArH), 7.05 (m, 1H, ArH), 11.57 (s, 1H, NH).

Step D. 5-Cyano-8-fluoro-1-propyl-1,3,4,9-tetrahydropyrano[3,4-b]indole-1-acetic acid ethyl ester Under an atmosphere of nitrogen, a mixture of the bromo compound of Step C (1.5 g, 3.9 mmol) and copper (I) cyanide (0.7 g, 7.8 mmol) in 20 mL of N-methyl-2-pyrrolidinone was heated at 170° C. for 5 h. Upon cooling the reaction mixture was partitioned between EtOAc and $H_2O$ and the resulting suspension was vacuum filtered (Celite) to remove dark solids. The clear layers were separated and the organic phase was washed 2 more times with $H_2O$ and brine. After drying ($Na_2SO_4$) the solvent was evaporated to provide 1.5 g of a brown oil which was purified by flash chromatography (silica Merck 60, hexane-EtOAc 3:1) to give 0.48 g of title product as a white solid.

NMR (DMSO-$d_6$, 400 MHz): δ 0.784 (m, 3H, $CCH_3$), 0.86 and 1.29 (m, 2H, $CCH_2C$), 1.007 (t, 3H, $OCH_2CH_3$), 1.92 (m, 2H, $CH_2C$), 2.76 (d, 1H, $CCH_2CO$), 2.86 (t, 2H, $CCH_2$), 3.02 (d, 1H, $CCH_2CO$), 3.9 (m, 4H, $CCH_2O$), 7.07 (m, 1H, ArH), 7.5 (m, 1H, ArH), 11.94 (s, 1H, NH).

MS (EI, m/z): 344 [M]$^+$, 301 [M–$C_3H_7$]$^+$, 257.

Step E. 5-Cyano-8-fluoro-1-propyl-1,3,4,9-tetrahydropyrano[3,4-b]indole-1-acetic acid A solution of the ester of Step D (0.46 g, 1.34 mmol) in 7 mL of ethanol and 3 mL of 1 N—NaOH was stirred at ambient temperature overnight. The solvent was evaporated and the residue partitioned between $Et_2O$ and $H_2O$. The aqueous phase was acidified with 1N—HCl and extracted with $Et_2O$. The organic phase was dried ($Na_2SO_4$) and the solvent removed to provide 0.46 g crude product. Crystallization from $Et_2O$-hexane afforded the title compound as a white solid (0.35 g, 82.5%).

NMR (DMSO-$d_6$, 400 MHz): δ 0.777 (m, 3H, $CCH_3$), 0.853 and 1.29 (m, 2H, $CH_2CH_2CH_3$), 1.97 (m, 2H, $CH_2C$), 2.685 (d, 1H, $CCH_2CO$), 2.86 (t, 2H, $CCH_2$), 2.93 (d, 1H, $CCH_2CO$), 3.9 (m, 2H, $CCH_2O$), 7.07 (m, 1H, ArH), 7.5 (m, 1H, ArH), 11.92 (s, 1H, NH), 12.03 (s, 1H, COOH).

MS [+CI, m/z]: 317 [M+H]$^+$

Anal. Calc'd for $C_{17}H_{17}FN_2O_3$: C, 64.55; H, 5.42; N, 8.86 Found: C, 64.07; H, 5.40; N, 8.57

EXAMPLE 2

5-Cyano-8-methyl-1propyl-1,3,4,9-tetrahydropyrano[3,4-b]indole-1acetic acid

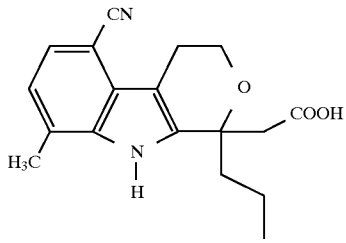

Step A. 4-(5-Bromo-2-methylphenyl hydrazono)-1-butanol

Under anhydrous conditions a solution of 5-bromo-2-methyl-phenylhydrazine hydrochloride (13.5 g, 57 mmol), 2,3-dihydrofuran (4.3 mL, 57 mmol) and sodium acetate (4.7 g, 57 mmol) in 200 mL of $CH_3OH$ was stirred at ambient temperature for 72 h. The reaction mixture was concentrated in vacuo and the residue partitioned between EtOAc and $H_2O$. The organic phase was washed with $H_2O$ and brine. After drying ($Na_2SO_4$), the solvent was evaporated to give 13.3 g of the title compound as a yellow oil. The crude product was used as was in the next step.

Step B. 4-Bromo-7-methyl tryptophol

Under an atmosphere of nitrogen, a mixture of the crude hydrazone of Step A (13.3 g, 49 mmol) and zinc chloride (13.3 g, 98 mmol) in 75 mL of ethylene glycol was heated at 160° C. for 5 h. Upon cooling the reaction mixture was partitioned between $Et_2O$ and dilute HCl. The organic phase was washed with $H_2O$ and brine. After drying ($Na_2SO_4$) the solvent was evaporated and the residue was purified by flash chromatography (silica Merck 60, hexane-EtOAc 3:1) to give 2.8 g of title product as a light brown oil.

NMR (DMSO-$d_6$, 300 MHz): δ 2.395 (s, 3H, $CH_3$), 3.05 (t, 2H, $ArCH_2C$), 3.65 (m, 2H, $OCH_2C$), 4.65 (t, 1H, OH), 6.9–7.5 (m, 4H, ArH), 11.1 (s, 1H, NH)

Step C. 5-Bromo-8-methyl-1propyl-1,3,4,9-tetrahydropyrano[3,4-b]indole-1-acetic acid ethyl ester Under anhydrous conditions, a solution of the tryptophol of Step B (2.3 g, 9.05 mmol) and ethyl 3-methoxy-2hexenoate (1.43 g, 9.05 mmol) in 30 mL of dry $CH_2Cl_2$ was treated dropwise with boron trifluoride etherate (1.11 mL, 9.05 mmol) via syringe. The solution was stirred at ambient temperature for 2 h and then washed with saturated aqueous $NaHCO_3$ and brine. Upon drying ($Na_2SO_4$), the organic phase was filtered through a pad of silica gel. The filter cake was washed with additional $CH_2Cl_2$ and the combined organic layer was evaporated to provide the title product as amber oil which solidified on standing (2.9 g).

NMR (DMSO-$d_6$, 400 MHz): δ 6 .768 (m, 3H, $CCH_3$), 0.829 (m, 1H, $CH_2C$), 1.05 (t, 3H, $OCH_2CH_3$), 1.29 (m, 1H, $CH_2C$), 1.95 (m, 2H, $CCH_2$), 2.775 (d, 1H, $CCH_2CO$), 2.95 (m, 2H, $CCH_2$), 3.01 (d, 1H, $CCH_2CO$), 3.9 (m, 4H, $CCH_2O$), 6.74 (d, 1H, ArH), 7.02 (d, 1H, ArH), 10.79 (s, 1H, NH).

MS [−FAB, m/z]: 393/395 [M]⁺, 416/418 [M+Na]⁺

Step D. 5-Cyano-8-methyl-1-propyl-1,3,4,9-tetrahydropyrano[3,4-b]indole-1-acetic acid ethyl ester Under an atmosphere of nitrogen, a solution of the bromo compound of Step C (2.75 g, 6.97 mmol) and copper (I) cyanide (1.25g, 13.95 mmol) in 30 mL of N-methyl-2pyrrolidinone was heated at 170° C. for 5 h. Upon cooling the reaction mixture was partitioned between EtOAc and $H_2O$. The mixture was vacuum filtered (Celite) to remove dark solids. The organic phase was washed two more times with $H_2O$ and brine. After drying ($Na_2SO_4$) the solvent was evaporated and the residue was purified by flash chromatography (silica, hexane-EtOAc 3:1) to give 1.4 g of title product as a white solid.

NMR (DMSO-$d_6$, 400 MHz): δ 0.796 (m, 3H, $CCH_3$), 0.83 (m, 1H, $CCH_2$), 1.042 (t, 3H, $OCH_2CH_3$), 1.2 (m, 1H, $CCH_2$), 1.95 (m, 2H, $CCH_2$), 1.95 (m, 2H, $CCH_2$), 2.52 (s, 3H, $CH_3$), 2.79 (d, 1H, $CCH_2CO$), 2.85 (m, 2H, $CCH_2$), 3.03 (d, 1H, $CCH_2CO$), 3.9 (m, 4H, $CCH_2O$), 6.98 (d, 1H, ArH), 7.35 (d, 1H, ArH), 11.158 (s, 1H, NH).

MS [+FAB, m/z]: 340 [M]⁺

Step E. 5-Cyano-8-methyl-1-propyl-1,3,4,9-tetrahydropyrano[3,4-b]indole-1-acetic acid A solution of the ester of Step D (1.05 g, 3.08 mmol) in 25 mL of ethanol and 6 mL of 1N—NaOH was stirred at ambient temperature overnight. The solvent was evaporated and the residue was partitioned between EtOAc and $H_2O$. The aqueous phase was acidified with 1N—HCl and the mixture was extracted with EtOAc. The organic phase was dried ($Na_2SO_4$) and the solvent removed in vacuo to provide 0.9 g crude product. Trituration with hot EtOAc afforded 0.68 g of the pure title compound, which was isolated as a 0.15 ethyl acetate solvate.

NMR (DMSO-$d_6$, 400 MHz): δ 0.773 (m, 3H, $CCH_3$), 0.82 (m, 1H, $CH_2C$), 1.29 (m, 1H, $CH_2C$), 1.95 (m, 2H, $CH_2C$), 2.52 (s, 3H, $CH_3$), 2.72 (d, 1H, $CCH_2CO$), 2.85 (m, 2H, $CCH_2$), 2.94 (d, 1H, $CCH_2CO$), 3.9 (m, 2H, $CCH_2O$), 6.98 (d, 1H, ArH), 7.35 (d, 1H, ArH), 11.14 (s, 1H, NH), 12.02 (s, 1H, COOH).

MS (+FAB, m/z): 313 [M+H]⁺, 335 [M+Na]⁺, 269 [M−$C_3H_7$]⁺, 253.

Anal. Calcd. for $C_{18}H_{20}N_2O_3$+0.15 mol EtOAc: C, 68.62; H, 6.56; N, 8.60 Found: C, 68.61; H, 6.40; N, 8.70.

EXAMPLE 3

5-Cyano-1-ethyl-1,3,4,9-tetrahydropyrano[3,4-b]indole-1-acetic acid

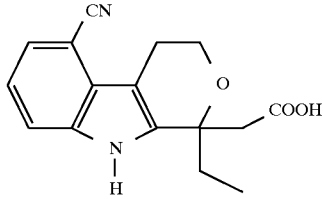

Step A. 4-(3-Bromo phenyl hydrazono)-1-butanol

Under anhydrous conditions a solution of 3-bromo-phenylhydrazine hydrochloride (22.5 g, 100 mmol) and 2,3-dihydrofuran (7.55 mL, 100 mmol) in 200 mL of dry THF was stirred at ambient temperature for 3 h. The reaction mixture was partitioned between EtOAc and $H_2O$. The organic phase was washed with $H_2O$ and brine. After drying ($Na_2SO_4$), the solvent was evaporated to give 25.6 g of the title product as a brown oil. The product was of suitable purity for use in the next step. NMR (DMSO-$d_6$, 300 MHz): δ 1.6 (m, 2H, $CH_2C$), 2.2 (m, 2H, $CHCH_2$), 3.15 (m, 2H, $CH_2OH$), 6.45 and 6.8 (m, 2H, vinyl H and ArH), 7.05 (m, 2H, ArH), 7.2 (m, 1H, ArH), 9.25 and 9.85 (s, 1H, NH).

Step B. 1:1 Mixture of 4-bromotryptophol and 6-bromotryptophol

Under an atmosphere of nitrogen, a mixture of the crude hydrazone of Step A (25.4 g, 98.8 mmol) and zinc chloride (27.2 g, 200 mmol) in 200 mL of ethylene glycol was heated at 160° C. for 3 h. Upon cooling the reaction mixture was partitioned between Et$_2$O and dilute HCl. The organic phase was washed with H$_2$O and brine, dried (Na$_2$SO$_4$), and evaporated to dryness. The more polar impurities were removed by filtering a solution of the crude product in CH$_2$Cl$_2$ through a pad of silica gel. Removal of the solvent afforded 22.7 g of a 1:1 mixture of 4- and 6-bromotryptophols as a brown oil.

NMR (DMSO-d$_6$, 300 MHz): $\partial$ 2.8 (t, 1H, ArCH$_2$C), 3.05 (t, 1H, ArCH$_2$C), 3.65 (m, 2H, OCH$_2$C), 6.9–7.5 (m, 4H, ArH), 10.9 (s, 0.5H, NH), 11.15 (s, 0.5H, (s 0.5, NH).

Step C. 5-Bromo-1-ethyl-1,3,4,9-tetrahydropyrano[3,4-b] indole-1-acetic acid methyl ester Under nitrogen, a solution of the 1:1 mixture of tryptophols of Step B (22.6 g, 94.1 mmol) and methyl 3-methoxy-2-pentenoate (13.5, 94.1 mmol) in 200 mL of dry CH$_2$Cl$_2$ was treated dropwise with boron trifluoride etherate (13.35 g, 94.1 mmol) via a syringe. The solution was stirred at ambient temperature for 2 h and then washed with saturated aqueous NaHCO$_3$ and brine. Upon drying (Na$_2$SO$_4$), the organic phase was filtered through a pad of silica gel. The filter cake was washed with additional CH$_2$Cl$_2$ and the combined organic layer was evaporated to provide 23 g of product as a mixture of regioisomers. Flash chromatography (silica, toluene-EtOAc, 9:1) of the mixture provided 1.4 g of the pure 5-bromo title compound. An additional 3.6 g of product were obtained by recrystallizing the recovered mixture of regioisomers from Et$_2$O-Petroleum ether and seeding with pure 5-bromo isomer.

NMR (DMSO-d$_6$, 400 MHz): δ 0.615 (t, 3H, CCH$_3$), 1.95 (q, 2H, CCH$_2$), 2.76 (d, 1H, CCH$_2$CO), 2.96 (m, 2H, CCH$_2$), 3.32 (s, 3H, OCH$_3$), 3.9 (m, 2H, CCH$_2$O), 6.93 (t, 1H, ArH), 7.11 (d, 1H, ArH), 7.32 ( d, 1H, ArH), 11.148 (s, 1H, NH)

MS (EI, m/z): 351/353 [M]$^+$, 322/324 [M–C$_2$H$_5$]$^+$, 278/280

Anal. Calcd. for C$_{16}$H$_{18}$BrNO$_3$: C, 54.56; H, 5.15; N, 3.98; Found: C, 54.34; H, 5.07; N, 3.98.

Alternatively, the 4-bromotryptophol of Example 4, Step D can be used as the starting material in a more efficient, regiospecific preparation of the compound of Step C.

Step D. 5-Cyano-1-ethyl-1,3,4,9-tetrahydropyrano[3,4-b] indole-1-acetic acid methyl ester Under an atmosphere of nitrogen, a solution of bromo compound of Step C (0.409 g, 1.26 mmol) and copper (I) cyanide (0.202 g, 2.27 mmol) in 10 mL of N-methyl-2-pyrrolidinone was heated at 170° C. for 5 h. Upon cooling the reaction mixture was partitioned between EtOAc and H$_2$O The mixture was vacuum filtered (Celite) to remove dark solids. The organic phase was washed two more times with H$_2$O and brine. After drying (Na$_2$SO$_4$) the solvent was evaporated to yield 0.500 g of crude solid. Further purification by flash chromatography (silica, hexane-EtOAc 2:1) provided 0.145 g of the title compound.

NMR (DMSO-d$_6$, 400 MHz): δ 0.642 (t, 3H, CCH$_3$), 1.958 (q, 2H, CCH$_2$C), 2.78 (d, 1H, CCH$_2$CO), 2.86 (m, 2H, CCH$_2$), 2.99 (d, 1H, CCH$_2$CO), 3.53 (s, 3H, OCH$_3$), 3.9 (m, 2H, CCH$_2$O), 7.18 (t, 1H, ArH), 7.44 (d, 1H, ArH), 7.66 ( d, 1H, ArH), 11.482 (s, 1H, NH).

MS (EI, m/z): 298 [M]$^+$, 269 [M–C$_2$H$_5$]$^+$, 225 [M–CH$_2$CO$_2$Me]$^+$, 195

Step E. 5-Cyano-1-ethyl-1,3,4,9-tetrahydropyrano[3,4-b] indole-1-acetic

A solution of the ester of Step D (0.14 g, 0.47 mmol) in 5 mL of ethanol and 1 mL of 1N—NaOH was stirred at ambient temperature overnight. The solvent was evaporated and the residue partitioned between Et$_2$O and H$_2$O. The aqueous phase was acidified with 1N—HCl. The mixture was extracted with Et$_2$O, the organic phase was dried (Na$_2$SO$_4$) and the solvent removed to provide 0.14 g of crude product. Recrystallization from Et$_2$O-petroleum ether afforded 0.114 g of the title compound as a white solid, as a 0.3 ethyl acetate solvate.

NMR (DMSO-d$_6$, 400 MHz): δ 0.649 (t, 3H, CCH$_3$), 1.96 (m, 2H, CCH$_2$C), 2.68 (d, 1H, CCH$_2$CO), 2.88 (m, 3H, CCH$_2$), 3.9 (m, 2H, CCH$_2$O), 7.17 (t, 1H, ArH), 7.44 (d, 1H, ArH), 7.66 ( d, 1H, ArH), 11.46 (s, 1H, NH), 12.05 (broad, 1H, COOH).

MS [EI, m/z]: 284 [M]$^+$, 255 [M–C$_2$H$_5$]$^+$, 225, 195

Anal. Calcd. for C$_{16}$H$_{16}$N$_2$O$_3$+0.3 mol EtOAc: C, 66.52; H, 5.96; N, 9.04; Found: C, 66.04; H, 5.90; N, 8.72.

EXAMPLE 4

5-Cyano-1-propyl-1,3,4,9-tetrahydropyrano[3,4-b] indole-1-acetic acid

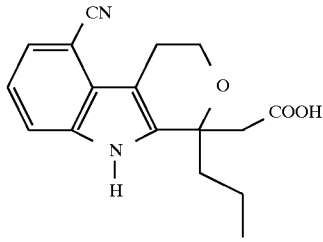

Step A. 4-Bromo indole

Essentially as described in J. Org, Chem. 1986, 51, 5106, a solution of 2-bromo-6-nitrotoluene (15.95 g, 74 mmol), dimethylformamide dimethyl acetal (26.7 mL, 220 mmol) and pyrrolidine (6.2 mL, 74 mmol) in 100 mL of DMF was heated at 110° C. for 3 h under an atmosphere of nitrogen. The cooled reaction mixture was diluted with Et$_2$O and washed with H$_2$O. The organic phase was dried (Na$_2$SO$_4$) and concentrated in vacuo to give the intermediate enamine as a dark red oil.

A mechanically stirred solution of this enamine (21.9 g) in 250 mL of 80% acetic acid heated to 75° C. was treated portionwise with zinc dust (41 g, 640 mmol). The reaction temperature was then raised to 85° C. and stirring was continued for an additional hour. The solids obtained upon cooling were filtered and the filtrate was partitioned between Et$_2$O and H$_2$O. The organic phase was washed with H$_2$O, saturated aqueous NaHCO$_3$, and brine, and dried (Na$_2$SO$_4$). Removal of solvent afforded 13 g of a dark purple oil. Flash chromatography of the residue (silica, CH$_2$Cl$_2$-hexane 1:1) gave the title product as a clear oil, 8.9 g.

NMR (DMSO-d$_6$, 200 MHz): δ 6.4 (m, 1H, ArH), 7.0 (t, 1H, ArH), 7.2 (d, 1H, ArH), 7.45 (m, 2H, ArH), 11.45 (broad, 1H, NH).

Step B. Ethyl 2-(4-bromo-3indoly)-glyoxalate

Under anhydrous conditions, oxalyl chloride (6.1 mL, 70 mmol) was added dropwise to a solution of the 4-bromoindole of Step A (5.5 g, 28 mmol) at −10° C. The cooling bath was removed and stirring was continued for 1 h. The mixture of yellow solids was concentrated in vacuo. The residue was dissolved in absolute ethanol and stirred overnight at ambient temperature. The solvent was evaporated in vacuo and the residue (purple solid) was purified by flash chromatography (silica, hexane-EtOAc 2:1) to give 4.08 g of the title compound as a white solid.

NMR (DMSO-d$_6$, 400mHz) $\partial$ 1.30 (t, 3H, CH$_2$CH$_3$), 4.33 (q, 2H, OCH$_2$CH$_3$), 7.19 (t, 1H, ArH), 7.45 (d, 1H, ArH), 7.54 (d, 1H, ArH), 8.36 (s, 1H, ArH) 12.63 (broad, 1H, NH).

MS (EI, m/z): 295/297 [M]$^+$, 222/224 [M–CO$_2$C$_2$H$_5$]$^+$, 115.

Anal. Calc'd for $C_{12}H_{10}BrNO_3$: C, 48.67; H, 3.40; N, 4.73 Found: C, 48.81; H, 3.19; N, 4.71

Step C. 4-Bromo tryptophol

Under anhydrous conditions, lithium aluminum hydride (LAH) (1.06 g, 27.9 mmol) was added portionwise to a solution of the glyoxalate of Step B (3.8 g, 13.97 mmol) in 50 mL of dry THF. The mixture was heated at reflux for 2 h. Excess LAH was decomposed by the stepwise addition of 1 mL $H_2O$, 1 mL 1N—NaOH, 3 mL $H_2O$. 12.5 g $Na_2SO_4$ was added and after stirring for 10 min, the solids were filtered and the filtrate was concentrated in vacuo to give 2.4 g of a light tan oil which solidified on standing.

NMR (DMSO-$d_6$, 400 MHz): δ 3.049 (t, 2H, ArCH$_2$C), 3.64 (m, 2H, OCH$_2$C), 6.93 (t, 1H, ArH), 7.13 (d, 1H, ArH), 7.23 (s, 1H, ArH), 7.35 (d, 1H , ArH), 11.17 (s, 1H, NH)

MS (EI, m/z): 239/241 [M$^+$, 1 Br present)], 208/210.

Step D. 5-Bromo-1-propyl-1,3,4,9-tetrahydropyrano3,4-b]indole-1-acetic acid ethyl ester Under anhydrous conditions, a solution of the 4-bromo tryptophol of Step C (3.4 g, 14.1 mmol) and ethyl 3-methoxy-2-hexenoate (2.23 g, 14.1 mmol) in 50 mL of dry $CH_2Cl_2$ was treated dropwise with boron trifluoride etherate (1.73 mL, 14.1 mmole) via syringe. The solution was stirred at ambient temperature for 2 h and then washed with saturated aqueous $NaHCO_3$ and brine. Upon drying ($Na_2SO_4$), the mixture (preabsorbed on silica gel) was purified by flash chromatography (silica hexane-EtOAc 4:1) to provide 2.9 g of the title compound as a clear oil.

NMR (DMSO-$d_6$, 400 MHz): δ 0.8 (m, 3H, CCH$_3$), 1.05 (t, 3H, OCH$_2$CH$_3$), 1.2 (m, 2H, CCH$_2$), 1.90 (m, 2H, CCH$_2$), 2.72 (d, 1H, CCH$_2$CO), 2.96 (m, 3H, CH$_2$), 3.95 (m, 4H, CCH$_2$O), 6.93 (t, 1, ArH), 7.11 (d, 1, ArH), 7.31 (d, 1H, ArH), 11.14 (s, 1H, NH)

MS (EI, m/z): 379/381 [M]$^+$, 336/338 [M-C$_3$H$_7$]$^+$, 292/294.

Step E. 5-Cyano-1-propyl-1,3,4,9-tetrahydropyrano[3,4-b]indole-1-acetic acid ethyl ester Under an atmosphere of nitrogen, a solution of the bromo compound of Step D (1.0 g, 2.73 mmol) and copper (I) cyanide (0.45 g, 5 mmol) in 10 mL of N-methyl-2-pyrrolidine was heated at 170° C. for 5 h. Upon cooling the reaction mixture was partitioned between EtOAc and $H_2O$. The slurry was vacuum filtered (Celite) to remove dark solids. The organic phase was washed two more times with $H_2O$ and brine. After drying ($Na_2SO_4$) the solvent was evaporated, and the residual oil (0.6 g,) was purified by flash chromatography (silica, hexane-EtOAc 2:1) to provide 0.32 g of the title compound as a white solid.

NMR (DMSO-$d_6$, 400 MHz): δ 0.778 (m, 3H, CCH$_3$), 0.85 (m, 1H, CH$_2$C), 1.02 (t, 3H, OCH$_2$CH$_3$), 1.30 (m, 1, CH$_2$C), 1.90 (m, 2H, CCH$_2$), 2.48 (d, 1H, CCH$_2$CO), 2.95 (m, 2H, CCH$_2$), 3.95 (m, 4H, CCH$_2$O), 7.17 (t, 1H, ArH), 7.44 (d, 1H, ArH), 7.65 ( d, 1H, ArH), 11.47 (s, 1H, NH).

MS (EI, m/z): 326 [M]$^+$, 283 [M-C$_3$H$_7$]$^+$, 239.

Step F. 5-Cyano-1-propyl-1,3,4,9-tetrahydropyrano[3,4-b]indole-1-acetic acid

A solution of the ester of Step E (0.31 g, 0.95 mmol) in 7 mL of ethanol and 2 mL of 1N—NaOH was stirred at ambient temperature overnight. The solvent was evaporated and the residue partitioned between $Et_2O$ and 1N—HCl. The organic phase was dried ($Na_2SO_4$) and concentrated to 5 mL. The crystalline product was filtered and dried to give 0.130 g of pure title compound as a white solid, mp 189°–190° C. NMR (DMSO-$d_6$, 400 MHz): δ 0.772 (m, 3H, CCH$_3$), 0.814 (m, 1H, CH$_2$C), 1.30 (m, 1H, CH$_2$C), 1.90 (m, 2H, CH$_2$C), 2.68 (d, 1H, CCH$_2$CO), 2.87 (m, 2H, CCH$_2$), 2.9 (d, 1H, CCH$_2$CO), 3.95 (m, 2H, CCH$_2$O), 7.17 (t, 1H, ArH), 7.43 (d, 1H, ArH), 7.645 ( d, 1H, ArH), 11.45 (s, 1H, NH), 12.06 (s, 1H, COOH).

MS (EI, m/z): 298 [M$^+$, 255 [M-C$_3$H$_7$]$^+$, 239.

EXAMPLE 5

1-Allyl-5-cyano-8-fluoro-2,3,4,9-tetrahydro-1H-carbazole-1-acetic acid

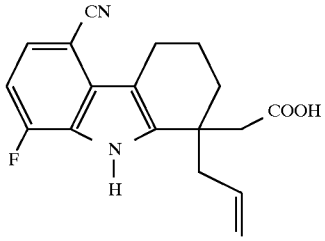

Step A. 1-Allyl-5-bromo-8-fluoro-2,3,4,9-tetrahydro-1H-carbazole-acetic acid methyl ester Under anhydrous conditions, a solution of 5-bromo-2-fluoro-phenylhydrazine hydrochloride (2 g, 8.28 mmole), 2-(1-allyl-2-cyclohexanonyl)acetic acid methyl ester (1.75 g, 8.28 mmole) and sodium acetate (1.02 g, 12.4 mmole) in 20 mL of MeOH was stirred at ambient temperature overnight. The reaction mixture was concentrated in vacuo and the residue partitioned between EtOAc and $H_2O$. The organic phase was washed with brine and dried ($MgSO_4$). The solvent was evaporated to provide 3.56 g of the hydrazone (mixture of E/Z isomers). A solution of the crude hydrazones and boron trifluoride etherate (1.23 g, 8.69 mmole) in 75 mL of glacial acetic acid was heated at 100° C. for 2 h. The reaction mixture was partitioned between $Et_2O$ and $H_2$. The organic phase was washed with $H_2O$, saturated aqueous $NaHCO_3$ and brine. The solvent was removed and the residue (preabsorbed on silica) was flash chromatographed (5% ethylacetate in hexane) to provide 1.17 g of the title product.

NMR (DMSO-$d_6$, 200 MHz): δ 1.71–2.97 (m, 1OH, CH$_2$), 3.51 (s, 3H, CH$_3$), 5.01 (m, 2H, C=CH$_2$), 5.49 (m, 1H, C=CH), 6.79 (dd, 1, ArH), 7.03 (dd, 1, ArH), 11.44 (s, 1H, NH)

MS (EI, m/z): 379/381 [M]$^+$

Step B. 1-Allyl-5-cyano-8-fluoro-2,3,4,9-tetrahydro-1H-carbazole-1-acetic acid methyl ester Under an atmosphere of nitrogen, a solution of the bromo intermediate of Step A (0.935 g, 2.44 mmol) and copper (I) cyanide (0.440 g, 4.9 mmol) in 12 mL of N-methyl-2pyrrolidinone methyl-2-pyrrolidinone was heated at 180° C for 5 h. Upon cooling, the reaction mixture was partitioned between EtOAc and $H_2O$. The mixture was filtered (Celite) to remove dark solids. The organic phase was washed twice with $H_2O$ and brine, dried ($MgSO_4$), and evaporated to dryness. The residue (preabsorbed on silica) was further purified by flash chromatography (hexane-EtOAc 3:1) to give the title compound as a white solid, mp 132°–134° C.

NMR (DMSO-$d_6$, 400 MHz): δ 8 1.74–2.89 (m, 1OH, CH$_2$C), 3.51 (s, 3H, CH$_3$), 5.02 (m, 2H, C=CH$_2$), 5.52 (m, 1H, CH=C), 7.03 (dd, 1H, ArH), 7.45 (dd, 1, ArH), 11.79 (s, 1H, NH).

MS (EI, m/z): 326 [M]$^+$

Anal. Calcd. for $C_{19}H_{19}FN_2O_2$: C, 69.92; H, 5.87; N, 8.58 Found : C, 69.59; H, 5.83; N, 8.45

Step C. 1-Allyl-5-cyano-8-fluoro-2,3,4,9-tetrahydro-1H-carbazole-1-acetic acid

A solution of the ester of Step B (0.500 g, 1.53 mmol) in 10 mL of methanol and 10 mL of 1N NaOH was stirred under nitrogen at 60° C. for one hour. The solvent was evaporated and the residue partitioned between CH$_2$Cl$_2$ and H$_2$O. The aqueous phase was acidified with 2N HCl and extracted with Et$_2$O. The organic phase was dried (MgSO$_4$) and the solvent removed to provide the crude product. Recrystallization of the residue from Et$_2$O-hexane to afford the title compound as a white solid (0.275 g, mp 218° C.).

NMR (DMSO-d$_6$, 400 MHz): ∂ 1.78–2.83 (m, 10H, CH$_2$C), 5.01 (m, 2H, C=CH$_2$), 5.54 ( m, 1H, CH=C), 7.02 (dd, 1, ArH), 7.43 (dd, 1H, ArH), 11.79 (s, 1H, NH), 12.06 (s, 1H, COOH).

MS (+FAB, m/z): 313 [M+H]$^+$, 335 [M+Na]$^+$

Anal. Calcd. for C$_{18}$H$_{17}$FN$_2$O$_2$: C, 69.22; H, 5.49; N, 8.97 Found : C, 69.02; H, 5.43; N, 8.91.

EXAMPLE 6

5-Cyano-8-fluoro-1-propyl-2,3,4,9-tetrahydro-1H-carbazole-1-acetic acid

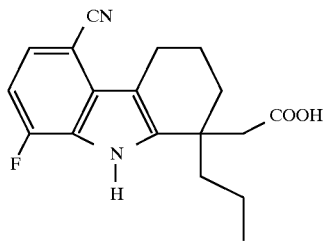

Step A. 5-Bromo-8-fluoro-1-propyl-2,3,4,9-tetrahydro-1H-carbazole-1-acetic acid methyl ester A solution of 5-bromo-2-fluoro-phenylhydrazine hydrochloride (2.88 g, 12.09 mmol), 2-(1-propyl-2-cyclohexanonyl)acetic acid methyl ester (2.44 g, 11.48 mmol) and sodium acetate (1.49 g, 18.14 mmol) in 30 mL of MeOH was stirred at ambient temperature under nitrogen overnight. The reaction mixture was concentrated in vacuo and the residue partitioned between Et$_2$O and H$_2$O. The organic phase was washed with brine and dried (MgSO$_4$). The solvent was evaporated to provide the intermediate hydrazone (mixture of E/Z isomers). A solution of the crude hydrazone and boron trifluoride etherate (1.89 g, 13.3 mmole) in 100 mL of glacial acetic acid was heated at 100° C. for 2 h. The reaction mixture was partitioned between EtOAc and H$_2$O. The organic phase was washed with H$_2$O, saturated aqueous NaHCO$_3$ and brine, and evaporated to dryness. The residue (preabsorbed on silica Merck-60) was flash chromatographed (2.5% ethyl acetate in hexane) to provide 2.18 g of the title compound.

NMR (DMSO-d$_6$, 300 MHz): δ 0.8 (m, 3H, CCH$_3$), 0.88–2.98 (m, 12H, CCH$_2$), 3.51 (s, 3H, CH$_3$), 6.77 (dd, 1, H ArH), 7.025 (dd, 1H, ArH), 11.36 (s, 1, NH)

MS (EI, m/z): 381/383 [M]$^+$

Step B. 5-Cyano-8-fluoro-1-propyl-2,3,4,9-tetrahydro-1H-carbazole-1-acetic acid methyl ester Under an atmosphere of nitrogen, a solution of the bromo compound of Step A (1 g, 2.62 mmol) and copper (I) cyanide (0.466 g, 5.23 mmol) in 10 mL of N-methyl-2-pyrrolidinone was heated at 175° C. for 2 h. Upon cooling the reaction mixture was partitioned between EtOAc and H$_2$O. The mixture was filtered (Celite) to remove dark solids. The organic phase was washed twice with H$_2$O and brine, dried (MgSO$_4$) and evaporated to dryness. The residue (preabsorbed on silica) was flash chromatographed (10% ethyl acetate in hexane) to give 0.51 g of the title compound as a white solid, mp 163°–165° C.

NMR (DMSO-d$_6$, 400 MHz): δ 0.8 (m, 3H, CCH$_3$), 0.92–2.86 (m, 12H, CCH$_2$C), 3.50 (s, 3H, OCH$_3$), 7.01 (dd, 1, ArH), 7.42 (dd, 1, ArH), 11.72 (s, 1, NH)

MS (EI, m/z): 328 [M]$^+$

Anal. Calcd. for C$_{19}$H$_{21}$FN$_2$O$_2$: C, 69.49; H, 6.45; N, 8.53 Found: C, 68.97; H, 6.28; N, 8.31

Step C. 5-Cyano-8-fluoro-1-propyl-2,3,4,9-tetrahydro-1H-carbazole-1-acetic acid

A solution of the ester of Step B (0.412 g, 1.25 mmol) in 5 mL of methanol and mL of 1N NaOH was stirred under nitrogen at room temperature overnight. The solvent was evaporated and the residue was partitioned between CH$_2$Cl$_2$ and H$_2$O. The aqueous phase was acidified with 2N HCl, and extracted with Et$_2$O. The organic phase was dried (MgSO$_4$) and the solvent removed. Recrystallization of the residue from EtOAc afforded the title compound as a white solid, mp 222°–223° C. (dec).

NMR (DMSO-d6, 400 MHz): δ 6 0.80 (m, 3H, CCH$_3$), 0.96–2.82 (m, 12H, CCH$_2$), 7.00 (dd, 1H, ArH), 7.43 (dd, 1H, ArH), 11.73 (s, 1H, NH), 12.02 (s, 1H, COOH)

MS [–FAB, m/z]: 313 [M–H]$^-$

Calcd. for C$_{18}$H$_{19}$FN$_2$O$_2$: C, 68.77; H, 6.09; N, 8.91 Found: C, 68.13; H, 6.07; N, 8.68

EXAMPLE 7

1-Allyl-5-cyano-8-methyl-2,3,4,9-tetrahydro-1H-carbazole-1-acetic acid

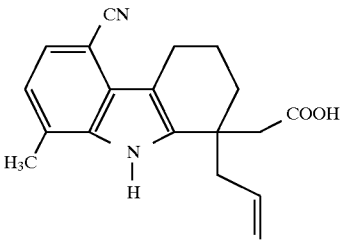

Step A. 5-Bromo-2-methyl aniline

A solution of 4-bromo-2-nitrotoluene (39 g, 0.18 mol) and stannous chloride dihydrate (203 g, 0.9 mol) in 400 mL of EtOAc was heated at 70° C. for 4 h. Upon cooling the reaction was poured into a mixture of ice and 160 mL of 50% NaOH. The solids were filtered and discarded. The organic phase was washed with H$_2$O and brine, dried (Na$_2$SO$_4$) and evaporated in vacuo to provide the title compound (27.4 g) as a yellow liquid.

NMR (DMSO-d$_6$, 300 MHz): ∂ 1.95 (s, 3H, CH$_3$), 5.125 (broad, 2H, NH$_2$), 6.55 (m, 1H, ArH), 6.65 (d, 1H, ArH), 6.825 (d, 1H, ArH).

Step B. 5-Bromo-2-methyl phenylhydrazine hydrochloride

A solution of sodium nitrite (10.3 g, 0.15 mol) in 50 mL of water was added dropwise to a mechanically stirred suspension of the 5-bromo-2-methyl aniline hydrochloride (27.4 g, 0.15 mol) of Step A in 6N HCl (300 mL) and glacial acetic acid (120 mL) maintained below 5° C. After stirring the mixture for 45 minutes at –5° C. a solution of stannous chloride dihydrate (67.7 g, 0.30 mole) in 100 mL of conc. HCl was added in one portion. The thick suspension was stirred an additional hour allowing the bath to warm to room temperature. The solids were filtered, washed with water and dried overnight in vacuo to afford 27.6 g of the title compound.

NMR (DMSO-d$_6$, 400 Mhz): δ 2.11 (s, 3H, CH$_3$), 7.03 (m, 2H, ArH), 7.11 (s, 1H, ArH), 8.106 (s, 1H, NH), 10.31 (s, 3H, NH$_3{}^+$)

MS [+CI, m/z]: 201/203 (M+H)+, 184/186

Step C. 2-[2-(5'-Bromo-2'-methylphenylhydrazono)-1-allyl-cyclohexan-1-yl]-acetic acid methyl ester Under a nitrogen atmosphere, a solution of 5-bromo-2-methyl phenylhydrazine hydrochloride of Step B (5 g, 21.1 mmol), 2-(1-allyl-2-cyclohexanonyl)acetic acid methyl ester (4.43 g, 21.1 mmol) and sodium acetate (2.6 g, 31.7 mmol) in 100 mL of MeOH was stirred at ambient temperature overnight. The reaction mixture was concentrated in vacuo and the residue partitioned between EtOAc and H$_2$O. The organic phase was washed with brine and dried (Na$_2$SO$_4$). The solvent was evaporated to provide 8.3 g of the product as a yellow oil (mixture of E/Z isomers), of sufficent purity to be used as such in the next step.

NMR (DMSO-d$_6$, 200 MHz): δ 1.3–2.2 (m, 8H, CH$_2$), 2.12 (s, 3H, CH$_3$), 2.35 (m, 3H, CH$_2$), 2.65 (d, 1H, CCH$_2$CO), 2.79 (m, 1H, CCH$_2$), 3.57 (s, 3H, OCH$_3$), 5.05 (m, 2H, C=CH$_2$), 5.70 (m, 1H, CH=C), 6.8 (d, 1, ArH), 6.95 (d, 1H, ArH), 7.35, (s, 1, ArH), 7.9 (s, 1H, NH).

Step D. 1-Allyl-5-bromo-8-methyl-2,3,4,9-tetrahydro-1-carbazole-1-acetic acid methyl ester Under a nitrogen atmosphere, a solution of the hydrazone of Step C (8.3 g, 21.1 mmol) and boron trifluoride etherate (2.6 mL, 21.1 mmol) in 50 mL of glacial acetic acid was heated at 100° C. for 2 h. The reaction mixture was partitioned between Et$_2$O and H$_2$O. The organic phase was washed with H$_2$O, saturated aqueous NaHCO$_3$ and brine. Removal of the solvent provided 5.6 g of the product as an amber solid, of sufficient purity to be used as such in the next step.

NMR (DMSO-d$_6$, 400 MHz): δ 1.7–1.9 (m, 4H, CH$_2$C), 2.4 (s, 3H, CH$_3$), 2.76 (d, 1H, CCH$_2$CO), 2.78 (m, 4H, CCH$_2$), 2.96 (m, 1H, CCH$_2$), 3.53 (s, 3H, OCH$_3$), 5.05 (m, 2H, C=CH$_2$), 5.7 (m, 1H, CH=C) 6.69 (d, 1H, ArH), 6.97 (d, 1H, ArH), 10.63 (s, 1H, NH).

MS (EI, m/z): 375/377 [M]+, 334/336 [M-C$_3$H$_5$]+, 302 [M-CH$_2$COOCH$_3$]+

Step E. 1-Allyl-5-cyano-8-methyl-2,3,4,9-tetrahydro-1H-carbazole-1-acetic acid methyl ester Under an atmosphere of nitrogen, a solution of the bromo intermediate of Step D (3 g, 7.9 mmol) and copper (I) cyanide (1.42 g, 15.8 mmol) in 50 mL of N-methyl-2-pyrrolidine was heated at 170° C. for 5 h. Upon cooling the reaction mixture was partitioned between EtOAc and H$_2$O. The mixture was vacuum filtered to remove dark solids. The organic phase was washed twice with H$_2$O and brine. After drying (Na$_2$SO$_4$) the solvent was evaporated to provide 4.6 g of a brown oil which was further purified by flash chromatography (silica, hexane-EtOAc 3:1) to give 0.95 g of title compound, along with unreacted starting bromide (1 g).

NMR (DMSO-d$_6$, 400 MHz): δ 1.74–1.97 (m, 4H, CH$_2$C), 2.45 (m, 2H, CH$_2$), 2.51 (s, 3H, CH$_3$), 2.78 (m, 4H, CCH$_2$), 3.53 (s, 3H, OCH$_3$), 5.05 (m, 2H, C=CH$_2$), 5.47 (m, 1H, CH=C), 6.94 (d, 1H, ArH), 7.30 (d, 1H, ArH), 10.98 (s, 1H, NH).

MS (EI, m/z): 322 [M]+, 281 [M-C$_3$H$_5$]+, 249 [M-CH$_2$COOCH$_3$]+

Step F. 1-Allyl-5-cyano-8-methyl-2,3,4,9-tetrahydro-1H-carbazole-1-acetic acid

A solution of the ester of Step E (0.85 g, 2.64 mmol) in 20 mL of ethanol and 5 mL of 1N NaOH was stirred at ambient temperature under nitrogen overnight. The solvent was evaporated and the residue partitioned between Et$_2$O and H$_2$O. The aqueous phase was acidified with 1N HCl and the mixture was extracted with Et$_2$O. The organic phase was dried (Na$_2$SO$_4$) and the solvent removed to provide 0.8 g of crude product. Recrystallization of the residue from EtOAc-hexane afforded the title compound as a white solid (0.275 g, mp–240°–241° C.).

NMR (DMSO-d$_6$, 400 MHz): δ 1.75 (m, 3H, CH$_2$C), 1.97 (m, 1H, CCH$_2$), 2.51 (s, 3H, CH$_3$), 2.62 (m, 1H, CCH$_2$CO), 2.78 (m, 3H, CCH$_2$), 5.05 (m, 2H, C=CH$_2$), 5.47 ( m, 1H, CH=C), 6.93 (d, 1H, ArH), 7.29 (d, 1H, ArH), 10.98 (s, 1H, NH), 12.06 (s, 1H, COOH).

MS (EI, m/z): 308 [M]+, 267 [M-C$_3$H$_5$]+, 249 [M-CH$_2$COOH]+.

Anal. Calcd. for C$_{19}$H$_{20}$N$_2$O$_2$: C, 74.00; H, 6.54; N, 9.08 Found: C, 73.74; H, 6.46; N, 8.97.

EXAMPLE 8

5-Cyano-1-propyl-8-methyl-2,3,4,9-tetrahydro-1H-carbazole-1-acetic acid

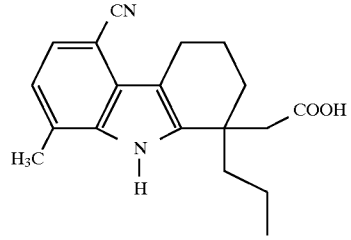

Step A. 2-[2-(5'-Bromo-2'-methylphenylhydrazono)-1-propylcyclohexan-1-yl]acetic acid methylester Under anhydrous conditions, a solution of the hydrazine hydrochloride of Example 7, Step A (1.83 g, 7.7 mmol), 2-(1-propyl-2-cyclohexanonyl)acetic acid methyl ester (1.63 g, 7.7 mmol) and sodium acetate (0.95 g, 11.5 mmol) in 50 mL MeOH was stirred at ambient temperature overnight. The reaction mixture was concentrated in vacuo and the residue partitioned between EtOAc and H$_2$O. The organic phase was washed with brine and dried (Na$_2$SO$_4$). The solvent was evaporated to provide 2.9 g of the product as a red oil (mixture of E/Z isomers) of sufficient purity to be used as such in the next step.

NMR (DMSO-d$_6$, 200 MHz): δ 0.85 (t, 3H, CH$_3$C), 1.3–2.2 (m, 1H, CH$_2$), 2.125 (s, 3H, ArCH$_3$), 2.4 (d, 1H, CCH$_2$CO), 2.65 (d, 1 H, CCH$_2$CO), 2.79 (m, 1H, CCH$_2$), 3.575 (s, 3H, OCH$_3$), 6.78 (d, 1H, ArH), 6.95 (d,1, ArH), 7.35, (s, 1H, ArH), 7.9, (s, 1H, NH).

Step B. 5-Bromo-8-methyl-1-propyl-2,3,4,9-tetrahydro-1H-carbazole-1-acetic acid methyl ester Under anhydrous conditions, a solution of the hydrazone of Step A (2.9 g, 7.3 mmol) and boron trifluoride etherate (0.95 mL, 7.7 mmol) in 20 mL of glacial acetic acid was heated at 100° C. for 2 h. The reaction mixture was and partitioned between Et$_2$O and H$_2$O. The organic phase was washed with H$_2$O, saturated aqueous NaHCO$_3$ and brine. Removal of the solvent provided 1.4 g of the product as a yellow oil, of sufficient purity to be used as such in the next step.

NMR (DMSO-d$_6$, 300 MHz): δ 0.8 (m, 3H, CCH$_3$), 0.95 and 1.2 (m, 2H, CCH$_2$C), 1.7–1.9 (m, 6H, CH$_2$C), 2.4 (s, 3H, CH$_3$), 2.75 (m, 4H, CCH$_2$), 3.53 (s, 3H, OCH$_3$), 6.8 (d, 1H, ArH), 7.15 (d, 1H, ArH), 10.25 (s, 1H, NH).

Step C. 5-Cyano-8-methyl-1-propyl-2,3,4,9-tetrahydro-1H-carbazole-1-acetic acid methyl ester Under an atmosphere of nitrogen, a solution of the bromo compound of Step B (1.35 g, 3.5 mmole) and copper (I) cyanide (0.64 g, 7.1 mmol) in 15 mL of N-methyl-2-pyrrolidinone was heated at 170° C for 5 h. Upon cooling the reaction mixture was partitioned between EtOAc and H$_2$O.

The mixture was vacuum filtered to remove dark solids. The organic phase was washed twice with H₂O and brine. After drying (Na₂SO₄) the solvent was evaporated to provide 1.0 g of a brown oil, which was purified by flash chromatography (silica, hexane-EtOAc 3:1) to give 0.23 g of the title compound.

NMR (DMSO-d₆, 300 MHz): δ 0.8 (m, 3H, CCH₃), 0.97 and 1.2 (m, 2H, CCH₂C), 1.6–2.0 (m, 6H, CH₂C), 2.55 (s, 3H, CH₃), 2.75 (m, 4H, CCH₂), 3.55 (s, 3H, OCH₃), 6.9 (d, 1H, ArH), 7.3 (d, 1H, ArH), 10.925 (s, 1H, NH).

Step D. 5-Cyano-8-methyl-1-propyl-2,3,4,9-tetrahydro-1H-carbazole-1-acetic acid

A solution of the ester of Step C (0.20 g, 0.61 mmol) in 7 mL of ethanol and 2 mL of 1N NaOH was stirred at ambient temperature overnight. The solvent was evaporated and the residue was partitioned between Et₂O and H₂O. The aqueous phase was acidified with 1N HCl, and extracted with Et₂O. The organic phase was dried (Na₂SO₄) and the solvent removed. Recrystallization of the residue from Et₂O-hexane affords the title compound as a pale pink solid (0.054 g).

NMR (DMSO-d₆, 400 MHz): δ 0.805 (m, 3H, CCH₃), 0.943 (m, 1H, CCH₂), 1.22 (m, 1H, CCH₂C), 1.66–1.92 (m, 5H, CH₂C), 2.01 (m, 1H, CCH₂), 2.51 (s, 3H, CH₃), 2.67 (q, 2H, CCH₂CO), 2.805 (m, 2H, CCH₂), 6.92 (d, 1H, ArH), 7.29 (d, 1H, ArH), 10.917 (s, 1H, NH), 12.016 (s, 1H, COOH).

MS [EI, m/z]: 310 [M]⁺, 267 [M-C₃H₇]⁺, 251.

EXAMPLE 9

8-Carboxamido-5-cyano-1-propyl-2,3,4,9-tetrahydro-1H-carbazole-1-acetic acid

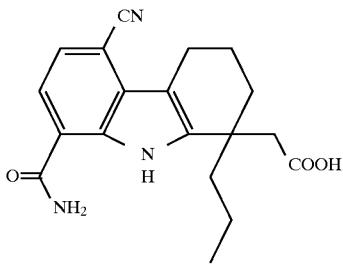

Step A. 2,5-Dibromo phenylhydrazine hydrochloride

A solution of sodium nitrite (6.9 g, 0.1 mol) in 50 mL of H₂O was added dropwise to a mechanically stirred suspension of 2,5-dibromoaniline (25 g, 0.1 mol) in 6N HCl (200 mL) and glacial acetic acid (80 mL) maintained below 5° C. After the addition was complete, the mixture was stirred for 45 min at −5° C. A solution of stannous chloride dihydrate (45.1 g, 0.2 mol) in 80 mL of conc. HCl was added in one portion to the thick suspension. Stirring was continued an additional hour allowing the bath to warm to ambient temperature. The solids were filtered, washed with H₂O and dried overnight in vacuo to afford 30 g of the title compound as an off white solid.

NMR (DMSO-d₆, 400 MHz): δ 7.07 (d, 1H, ArH), 7.26 (s, 1, ArH), 7.50 (d, 1H, ArH), 8.12 (s, 1H, NH), 10.205 (broad, 3H, NH3⁺).

MS (+FAB, m/z): 264/266/268 [M]⁺.

Step B. 2-[2-(2',5'-dibromophenylhydrazono)-1-popylcyclohexan-1-yl]acetic acid methyl ester Under anhydrous conditions, a solution of the phenylhydrazine hydrochloride of Step A (5.0 g, 15.6 mmol), 2-(1-propyl-2-cyclohexanonyl)acetic acid methyl ester (3.3 g, 16.5 mmol) and sodium acetate (1.9 g, 23.4 mmol) in 75 mL of MeOH was stirred at ambient temperature overnight. The reaction mixture was concentrated in vacuo and the residue partitioned between EtOAc and H₂O. The organic phase was washed with brine and dried (Na₂SO₄). The solvent was evaporated to provide 6.8 g of the title compound as an amber oil (mixture of E/Z isomers) of sufficient purity to be used as such in the next step.

NMR (DMSO-d₆, 400 MHz): δ .835 (m, 3H, CH₃C), 1.314 2.2 (m, 11H, CH₂), 2.4 (m, 2H, CH₂), 2.67 (d, 1H, CCH₂CO), 3.52–3.56 (s, 3H, OCH₃), 6.845 (m, 1H, ArH), 7.4 (d, 1H, ArH), 7.52, (s, 1H, ArH), 8.07, (s, 1H, NH).

MS (+FAB, m/z): 459/461/463 [M+H]⁺

Step C. 5,8-Dibromo-1-propyl-2,3,4,9-tetrahydro-1H-carbazole-1-acetic acid methyl ester Under a nitrogen atmosphere, a solution of the hydrazone of Step B (6.7 g, 14.6 mmol) and boron trifluoride etherate (1.8 mL, 15.3 mmol) in 50 mL of glacial acetic acid was heated at 100° C. for 2 h. The reaction mixture was partitioned between Et₂O and H₂O. The organic phase was washed with H₂O, saturated aqueous NaHCO₃ and brine. Removal of the solvent in vacuo provided 5.6 g of product as an amber oil.

NMR (DMSO-d₆, 400 MHz): δ 0.817 (m, 3H,CCH₃), 0.91 (m, 1, CCH₂), 1.2 (m, 1H, CCH₂C), 1.58–1.95 (m, 6H, CH₂C), 2.76 (d, 1H, CCH₂CO), 2.85–3.0 (m, 3H, CH₂), 3.524 (s, 3H, OCH₃), 7.03 (d, 1H, ArH), 7.11 (d, 1H, ArH), 10.89 (s, 1H, NH).

MS (+FAB, m/z): 442/444/446 [M+H]⁺

Step D. 5,8-Dicyano-1-propyl-2,3,4,9-tetrahydro-1H-carbazole-1-acetic acid methyl ester Under an atmosphere of nitrogen, a solution of the bromide intermediate of Step C (1.65 g, 3.72 mmol) and copper (I) cyanide (1.33 g, 14.9 mmol) in 25 mL of N-methyl-2-pyrrolidinone was heated at 170° C. for 5 h. Upon cooling, the reaction mixture was partitioned between EtOAc and H₂O. The mixture was vacuum filtered to remove dark solids. The layers were separated and the organic phase was washed twice with H₂O and brine. After drying (Na₂SO₄), the organic phase was filtered through a plug of silica Merck 60. The gel was washed with an additional portion of EtOAc. The combined eluates were evaporated to give 0.4 g of a yellow oil, which was recrystallized from EtOAc/hexane to provide 0.20 g of the title compound as an off white solid.

NMR (DMSO-d₆, 400 MHz): δ 0.812 (m, 3H, CCH₃), 0.95 (m, 1H, CCH₂C), 1.2 (m, 1H, CCH₂C), 1.67 (m, 1H, CH₂), 1.8–1.95 (m, 5H, CH₂C), 2.725 (d, 1H, CCH₂CO), 2.84 (m, 2H, CH₂), 2.89 (d, 1H, CCH₂CO), 3.507 (s, 3H, OCH₃), 7.55 (d, 1H, ArH), 7.63 (d, 1H, ArH), 12.13 (s, 1H, NH).

MS (EI, m/z): 335 [M]⁺, 292 [M-C₃H₇]⁺, 262.

Step E. 8-Carboxamido-5-cyano-1-propyl-2,3,4,9-tetrahydro-1H-carbazole-1-acetic acid A solution of the ester of Step D (0.178 g, 0.53 mmol) in 7 mL of THF and 1 mL of 1N LiOH was stirred at ambient temperature under nitrogen for 72 hours. The solvent was evaporated and the residue partitioned between Et₂O and 1 N HCl. The organic phase was washed with brine and dried (Na₂SO₄). The solvent was removed in vacuo and the residue was recrystallized from Et₂O to provide the title compound as a white solid.

NMR (DMSO-d₆, 400 MHz): δ 0.831 (m, 3H, CCH₃), 1.12 (m, 1H, CCH₂C), 1.228 (m, 1H, CCH₂C), 1.8 (m, 6H, CH₂), 2.67 (s, 2H, CCH₂CO), 2.83 (m, 2H, CH₂), 7.48 (d, 1H, ArH), 7.64 (m, 2H, ArH and NH₂), 8.23 (s, 1H, NH₂), 11.19 (s, 1H, NH), 12.32 (broad, 1H, COOH).

MS (EI, m/z): 338.1 [M−H]⁻

Anal. Calcd. for C₁₉H₂₁N₃O₂: C, 67.27; H, 6.24; N, 12.38 Found: C, 67.08; H, 6.18; N, 12.15.

EXAMPLE 10

5-Cyano-1-propyl-2,3,4,9-tetrahydro-1H-carbazole-1-acetic acid

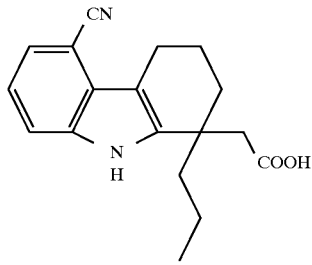

Step A. 2-[2-(3'-Bromophenylhydrazono)-1-propylcyclohexan-1-yl]acetic acid methyl ester

Under anhydrous conditions, a solution of 3-bromophenylhydrazine hydrochloride (5.0 g, 22.1 mmol), 2-(1-propyl-2-cyclohexanonyl) acetic acid methyl ester (4.7 g, 22.1 mmol) and sodium acetate (2.7 g, 33.1 mmol) in 100 mL of MeOH was stirred at ambient temperature for 4 h. The reaction mixture was concentrated in vacuo and the residue was partitioned between EtOAc and $H_2O$. The organic phase was washed with brine and dried ($Na_2SO_4$). The solvent was evaporated to provide 8.0 g of product as a red oil (mixture of E/Z isomers), of sufficient purity to be used as such in the next step.

Step B. 1:1 Mixture of 5-bromo- and 7-bromo-1-propyl-2,3,4,9-tetrahydro-1H-carbazole-1-acetic acid methyl ester

Under a nitrogen atmosphere, a solution of the hydrazone of Step A (8.0 g, 21 mmol) and boron trifluoride etherate (2.81 mL, 22.9 mmol) in 60 mL of glacial acetic acid was heated at 100° C. for 1.5 h. The reaction mixture was partitioned between $Et_2O$ and $H_2O$. The organic phase was washed three times with $H_2O$, saturated aqueous $NaHCO_3$ and brine. Removal of the solvent gives 7.0 g of a red oil which was further purified by flash chromatography (silica, hexane-EtOAc 4:1) to provide 1.1 g of the 7-bromo isomer (~95% pure) and 4.2 g of a 3:2 mixture of 5- and 7-bromo isomers, respectively.

[7-Bromo-1-propyl-1,2,3,4-tetrahydrocarbazol-1-yl]acetic acid methyl ester

NMR (DMSO-$d_6$, 400 MHz): δ 0.8 (m, 3H, $CCH_3$), 0.91 (m, 1H, $CCH_2C$), 1.2 (m, 1H, $CCH_2C$), 1.58–1.95 (m, 6H, $CH_2C$), 2.3–2.7 (m, 4H, $CH_2$), 3.5 (s, 3H, $OCH_3$), 7.03 (d, 1H, ArH), 7.225 (d, 1H, ArH), 7.4 (s, 1H, ArH), 10.8 (s, 1H, NH).

3:2 Mixture of 5-bromo-1-propyl-1,2,3,4-tetrahydrocarbazol-1-yl]- and 7-bromo-1-propyl-1,2,3,4-tetrahydrocarbazol-1-yl]acetic acid methyl esters

NMR (DMSO-$d_6$, 400 MHz): δ0.8 (m, 3H, $CCH_3$), 0.95 (m, 1H, $CCH_2C$), 1.2 (m, 1H, $CCH_2C$), 1.6–1.95 (m, 6H, $CH_2C$), 2.3–3.0 (m, 4H, $CH_2$), 3.5 (s, 3H, $OCH_3$), 6.875 (t, 0.6H, ArH), 7.05 (m, 1, ArH), 7.275 (m, 1H, ArH), 7.4 (s, 0.4H, ArH), 10.8 (s, 0.4H, NH), 10.95 (s, 0.6H, ArH).

Step C. 3:2 Mixture of 5-cyano-1-propyl- and 7-cyano-1-propyl-2,3,4,9-tetrahydro-1H-carbazole-1-acetic acid methyl esters

Under an atmosphere of nitrogen, a solution of the 3:2 mixture of the corresponding bromo esters of Step B (4.2 g, 11.5 mmol) and copper (I) cyanide (2.06 g, 23 mmol) in 25 mL of N-methyl-2-pyrrolidinone was heated at 170° C. for 5 h. Upon cooling the reaction mixture was partitioned between EtOAc and $H_2O$ and the suspension was vacuum filtered to remove dark solids. The organic phase was washed twice with $H_2O$ and brine. After drying ($Na_2SO_4$), the solvent was evaporated to give 4 g of crude material which was triturated with $Et_2O$ to provide a mixture of the title compounds (2.6 g) as a white solid.

NMR (DMSO-$d_6$, 400 MHz): δ 0.8 (m, 3H, $CCH_3$), 0.99 (m, 1, $CCH_2C$), 1.21 (m, 1H, $CCH_2C$), 1.6–1.92 (m, 6H, $CH_2C$), 2.5–2.9 (m, 4H, $CH_2$), 3.52 (s, 3H, $OCH_3$), 7.12 (t, 0.6H, ArH), 7.25 (d, 0.4H, ArH), 7.38 (d, 0.6H, ArH), 7.5 (d, 0.4H, ArH), 7.595 (d, 0.6H, ArH), 7.71 (s, 0.4H, ArH), 10.8 (s, 0.4H, NH), 11.26 (s, 0.4H, ArH), 11.296 (s, 0.6H, NH).

MS (EI, m/z): 310 $[M]^+$

Step D. 5-Cyano-1-propyl-2,3,4,9-tetrahydro-1H-carbazole-1-acetic acid

A solution of 3:2 mixture of esters of Step C (2.5 g, 8.05 mmol) in 50 mL of ethanol and 10 mL of 1N NaOH was stirred under nitrogen at ambient temperature overnight. The solvent was evaporated and the residue was partitioned between EtOAc and $H_2O$. The aqueous phase was acidified with 1N HCl and the mixture was extracted with EtOAc. The organic phase was dried ($Na_2SO_4$) and the solvent removed to provide 2.4 g of a crude mixture of 5- and 6-cyano acetic acids. Recrystallization from EtOAc afforded the pure 5-cyano title compound (0.55 g, mp 198° C., white solid), which was isolated as a 0.15 ethyl acetate solvate.

NMR (DMSO-$d_6$, 400 MHz): δ 0.8049 (m, 3H, $CCH_3$), 1.00 (m, 1H, $CCH_2C$), 1.21 (m, 1H, $CCH_2C$), 1.68–1.9 (m, 5H, $CH_2C$), 1.97 (m, 1H, $CH_2C$), 2.60 (q, 2H, $CCH_2CO$), 2.82 (m, 2H, $CH_2$), 7.11 (t, 1H, ArH), 7.37 (d, 1, ArH), 7.58 (d, 1H, ArH), 11.30 (s, 1H, NH), 12.05 (s, 1H, COOH).

MS (EI, m/z): 296 $[M]^+$, 253 $[M-C_3H_7]^+$, 237

Anal. Calcd. for $C_{18}H_{20}N_2O_2$+0.15 EtOAc: C, 72.16; H, 6.90;N, 9.05 Found: C, 72.20; H, 6.86;N, 9.03.

EXAMPLE 11

1-Allyl-5,8-dicyano-2,3,4,9-tetrahydro-1H-carbazole-1-acetic acid

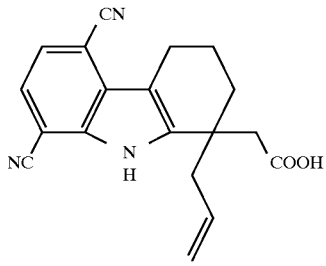

Step A. 2-[1-Allyl-2-(2'-5'-Dibromophenylhydrazono)-cyclohexan-1-yl]acetic acid methyl ester

Under anhydrous conditions, a solution of 2,5-dibromo phenylhydrazine hydrochloride of Example 9, Step A (5.0 g, 15.6 mmol), 2-(1-allyl-2-cyclohexanonyl)acetic acid methyl ester (3.5 g, 16.5 mmol) and sodium acetate (2.0 g, 24.8 mmol) in 75 mL MeOH was stirred at ambient temperature overnight. The reaction mixture was concentrated in vacuo and the residue was partitioned between EtOAc and $H_2O$. The organic phase was washed with brine and dried ($Na_2SO_4$). The solvent was evaporated to provide 7.05 g of the title compound as a mixture of E/Z isomers, of sufficient purity to be used as such in the next step.

NMR (DMSO-$d_6$, 400 MHz): δ 1.4–2.35 (m, 10H, $CH_2$), 2.65 (d, 1$CCH_2CO$), 2.79, m, 1H, $CCH_2$), 3.52+3.56 (s, 3H,

OCH₃), 5.05 (m, 2H, C=CH₂), 5.7 (m, 1H, CH=C), 6.85 (d, 1H, ArH), 7.39 (d,1, ArH), 7.52, (s, 1, ArH), 8.07 (s, 1H, NH).

MS (+FAB, m/z): 456.9/458.9/460.9 [M+H]⁺

Step B. 1-Allyl-5,8-dibromo-2,3,4,9-tetrahydro-1-H-carbazole-1-acetic acid methyl ester Under a nitrogen atmosphere, a solution of the hydrazone of Step A (7.0 g, 15.3 mmol) and boron trifluoride etherate (1.9 mL, 15.3 mmol) in 50 mL of glacial acetic acid was heated at 100° C. for 2 h. The reaction mixture was partitioned between Et₂O and H₂O. The organic phase was washed with H₂O, saturated aqueous NaHCO₃ and brine. Removal of the solvent provided 5.7 g of title product as an amber oil.

NMR (DMSO-d₆, 400 MHz): δ 1.7–2.96 (m, 10H, CH₂C), 3.53 (m, 3H, OCH₃), 5.05 (m, 2H, C=CH₂), 5.45 ( m, 1H, CH=C), 7.04 (d, 1H, ArH), 7.12 (d, 1H, ArH), 10.97 (s, 1H, NH).

MS (+FAB. m/z): 440/442/444 [M+H]⁺

Step C. 1-Allyl-5,8,dicyano-2,3,4,9-tetrahydro-1H-carbazole-1-acetic acid methyl ester Under an atmosphere of nitrogen, a solution of the bromide intermediate of Step B (1.62 g,3.67 mmol) and copper (I) cyanide (1.31 g, 14.7 mmol) in 25 mL of N-methyl-2-pyrrolidinone was heated at 170° C. for 5 h. Upon cooling, the reaction mixture was partitioned between EtOAc and H₂O. The mixture was vacuum filtered (Celite) to remove dark solids. The organic phase was washed twice with H₂O and brine. After drying (Na₂SO₄) the solvent was evaporated to give a brown oil, which was purified by flash chromatography (silica gel) to provide 0.42 g of title compound of sufficient purity to be used in the next step.

NMR (DMSO-d₆, 400 MHz): δ 1.67–1.96 (m, 6H, CH₂C), 2.76–2.84 (m, 3H, CCH₂), 2.95 (d, 1H, CCH₂CO), 3.50 (m, 3H, OCH₃), 5.05 (m, 2H, C=CH₂), 5.45 (m, 1H, CH=C), 7.56 (d, 1H, ArH), 7.64 (d, 1H, ArH), 12.19 (s, 1H, NH).

MS (+FAB. m/z): 334 [M+H]⁺, 332

Step D. 1-Allyl-5,8-dicyano-2,3,4,9-tetrahydro-1H-carbazole-1-acetic acid

A solution of the ester of Step C (0.35 g, 1.05 mmol) in 7 mL of ethanol and 2 mL of 1N NaOH was stirred at ambient temperature under nitrogen overnight. The solvent was evaporated and the residue was partitioned between EtOAc and H₂O. The aqueous phase was acidified with 1N HCl and the mixture was extracted with EtOAc. The organic phase was dried (Na₂SO₄) and the solvent removed in vacuo. The resulting solids were purified by preparative HPLC (C18 8μ 22×250 mm column, CH₃OH—H₂O—HOAc 65:53:0.1, flowrate=8 mL/min) to give 0.11 g of the title compound as a light yellow solid, which was isolated as a hemihydrate.

NMR (DMSO-d₆, 400 MHz): δ 1.82 (m, 3H, CH₂C), 1.96 (m, 1H, CCH₂), 2.60 (d, 1H, CCH₂CO), 2.707 (m, 1H, CCH₂), 2.825 (m, 2H, CH,), 2.88 (d, 1H, CCH₂CO), 5.02 (m, 2H, CH=CH,), 5.55 ( m, 1H, CH=CH₂), 7.55 (d, 1H, ArH), 7.63 (d, 1H, ArH), 12.09 (broad, 1H, NH), 12.29 (broad, 1H, COOH).

MS (EI, m/z): 319 [M]⁺, 278 [M–C₃H₅]⁺, 260

Anal. Calcd. for C₁₉H₁₇N₃O₂+0.5 mol H₂O: C, 69.50; H, 5.53;N, 12.80 Found: C, 69.76; H, 5.19;N, 12.35.

EXAMPLE 12

5,8-Dicyano-1-propyl-2,3,4,9-tetrahydro-1H-carbazole-1-acetic acid

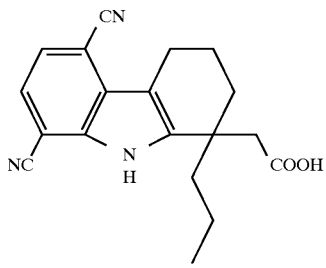

The mother liquors from the recrystallization of 1-propyl-5-cyano-8-carboxamido-2,3,4,9-tetrahydro-1-carbazole-1-acetic acid of Example 9, Step E were subjected to purification by preparative HPLC (C18 8μ 22×250 mm column, CH₃OH—H₂O-glacial HOAc 65:35:0.1, flowrate 8 mL/min) to give 0.080 g of the title compound as a light yellow solid.

NMR (DMSO-d₆, 400 MHz): ∂ 0.8137 (m, 3H, CCH₃), 1.02–2.83 (m, 12H, CCH₂), 7.55 (d, 1H, ArH), 7.62 (d, 1H, ArH), 12.056 (s, 1H, NH), 12.16 (broad, 1H, COOH).

MS (EI, m/z): 321 [M]⁺, 278 [M–C₃H₅]⁺, 262

EXAMPLE 13

7-Cyano-1-propyl-2,3,4,9-tetrahydro-1H-carbazole-1-acetic acid

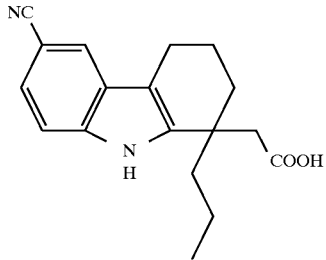

The mother liquors remaining from the isolation of 1-propyl-5-cyano-2,3,4,9-tetrahydro-1-carbazole-1-acetic acid of Example 11, Step D were concentrated in vacuo to give 2.0 g of a white solid. The title compound was isolated from this mixture by preparative HPLC (C18 8μ 22×250 mm column, CH₃OH—H₂O-glacial HOAc-70:30:0.1, flowrate 10 mL/min) as a white solid.

NMR (DMSO-d₆, 400 MHz): ∂ 0.803 (m, 3H, CCH₃), 1.01 (m, 1H, CCH₂), 1.20 (m, 1H, CCH₂), 1.7–1.82 (m, 5H, CH₂C), 1.99 (m, 1H, CH₂C), 2.60 (m, 4H, CCH₂), 7.24 (d, 1H, ArH), 7.485 (d, 1H, ArH), 7.70 (s, 1H, ArH), 11.26 (s, 1H, NH), 12.03 (s, 1H, COOH).

MS (EI, m/z): 296 [M]⁺, 253 [M–C₃H₇]⁺, 237

Anal. Calcd. for C₁₈H₂₀N₂O₂: C, 72.95; H, 6.80;N, 9.45 Found: C, 72.63; H, 6.63;N, 9.27.

What is claimed is:

1. A compound of formula I having the structure

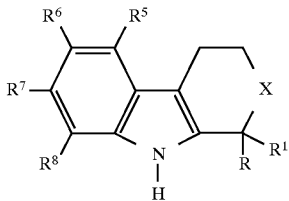

wherein
R is $(CH_2)_n COOR^4$;
$R^1$ is hydrogen, alkyl of 1–6 carbon atoms, alkenyl of 2–7 carbon atoms, alkynyl of 2–7 carbon atoms, alkylcycloalkyl of 4–14 carbon atoms, and alkoxyalkyl of 2–12 carbon atoms;
$R^4$ is hydrogen or alkyl of 1–6 carbon atoms;
$R^5$, $R^6$, $R^7$, and $R^8$ are each, independently, hydrogen, halogen, alkyl of 1–6 carbon atoms, alkenyl of 2–7 carbon atoms, alkynyl of 2–7 carbon atoms, alkoxy of 1–6 carbon atoms, arylalkoxy of 7–12 carbon atoms, fluoroalkoxy of 1–6 carbon atoms, alkylthio of 1–3 carbon atoms, alkylsulfinyl of 1–3 carbon atoms, alkylsulfonyl of 1–3 carbon atoms, cyano, nitro, —$SCF_3$, —$COR^3$, alkanoyloxy of 2–6 carbon atoms, hydroxy, trifluoromethyl, amino, alkylamino of 1–6 carbon atoms, dialkylamino in which each alkyl moiety is of 1–6 carbon atoms, alkylamido of 2–7 carbon atoms, or alkylsulfonamido of 1–6 carbon atoms;
wherein at least one of $R^5$, $R^6$, $R^7$, or $R^8$ is cyano;
$R^3$ is alkyl of 1–6 carbon atoms, hydroxy, alkoxy of 1–6 carbon atoms, amino, alkylamino of 1–6 carbons or dialkylamino in which each alkyl moiety is of 1–6 carbon atoms;
X is —C—; and
n=1–4
or a pharmaceutically acceptable salt thereof.

2. The compound according to claim 1, wherein $R^1$ is alkyl of 1–6 carbon atoms, or alkenyl of 2–7 carbon atoms or a pharmaceutically acceptable salt thereof.

3. The compound according to claim 2, wherein n=1 or a pharmaceutically acceptable salt thereof.

4. The compound according to claim 3, wherein $R^5$ is cyano or a pharmaceutically acceptable salt thereof.

5. The compound according to claim 1, which is 1-allyl-5-cyano-8-fluoro-2,3,4,9-tetrahydro-1H-carbazole-1-acetic acid or a pharmaceutically acceptable salt thereof.

6. The compound according to claim 1, which is 5-cyano-8-fluoro-1-propyl-2,3,4,9-tetrahydro-1-carbazole-1-acetic acid or a pharmaceutically acceptable salt thereof.

7. The compound according to claim 1, which is 1-allyl-5-cyano-8-methyl-2,3,4,9-tetrahydro-1H-carbazole-1-acetic acid or a pharmaceutically acceptable salt thereof.

8. The compound according to claim 1, which is 5-cyano-1-propyl-8-methyl-2,3,4,9-tetrahydro-1H-carbazole-1-acetic acid or a pharmaceutically acceptable salt thereof.

9. The compound according to claim 1, which is 8-carboxamido-5-cyano-1-propyl-2,3,4,9-tetrahydro-1H-carbazole-1-acetic acid or a pharmaceutically acceptable salt thereof.

10. The compound according to claim 1, which is 5-cyano-1-propyl-2,3,4,9-tetrahydro-1H-carbazole-1-acetic acid or a pharmaceutically acceptable salt thereof.

11. The compound according to claim 1, which is 1-allyl-5,8-dicyano -2,3,4,9-tetrahydro-1H-carbazole-1-acetic acid or a pharmaceutically acceptable salt thereof.

12. The compound according to claim 1, which is 5,8-dicyano-1-propyl-2,3,4,9-tetrahydro-1H-carbazole-1-acetic acid or a pharmaceutically acceptable salt thereof.

13. The compound according to claim 1, which is 7-cyano-1-propyl-2,3,4,9-tetrahydro-1H-carbazole-1-acetic acid or a pharmaceutically acceptable salt thereof.

14. A pharmaceutical composition which comprises a compound of formula 1 having the structure

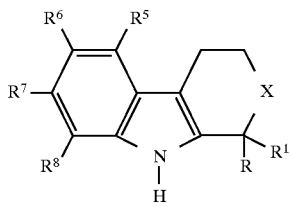

wherein
R is $(CH_2)_n COOR^4$;
$R^1$ is hydrogen, alkyl of 1–6 carbon atoms, alkenyl of 2–7 carbon atoms, alkynyl of 2–7 carbon atoms, alkylcycloalkyl of 4–14 carbon atoms, and alkoxyalkyl of 2–12 carbon atoms;
$R^4$ is hydrogen or alkyl of 1–6 carbon atoms;
$R^5$, $R^6$, $R^7$, and $R^8$ are each, independently, hydrogen, halogen, alkyl of 1–6 carbon atoms, alkenyl of 2–7 carbon atoms, alkynyl of 2–7 carbon atoms, alkoxy of 1–6 carbon atoms, arylalkoxy of 7–12 carbon atoms, fluoroalkoxy of 1–6 carbon atoms, alkylthio of 1–3 carbon atoms, alkylsulfinyl of 1–3 carbon atoms, alkylsulfonyl of 1–3 carbon atoms, cyano, nitro, —$SCF_3$, —$COR^3$, alkanoyloxy of 2–6 carbon atoms, hydroxy, trifluoromethyl, amino, alkylamino of 1–6 carbon atoms, dialkylamino in which each alkyl moiety is of 1–6 carbon atoms, alkylamido of 2–7 carbon atoms, or alkylsulfonamido of 1–6 carbon atoms; wherein at least one of $R^5$, $R^6$, $R^7$, or $R^8$ is cyano;
$R^3$ is alkyl of 1–6 carbon atoms, hydroxy, alkoxy of 1–6 carbon atoms, amino, alkylamino of 1–6 carbons or dialkylamino in which each alkyl moiety is of 1–6 carbon atoms;
X is —C—; and
n=1–4
or a pharmaceutically acceptable salt thereof and a pharmaceutical carrier.

* * * * *